United States Patent
Plant et al.

(10) Patent No.: US 7,419,936 B2
(45) Date of Patent: *Sep. 2, 2008

(54) OPTICALLY ACTIVE 2,5-BISARYL-$\Delta^1$-PYRROLINES AND THEIR USE AS PEST CONTROL AGENTS

(75) Inventors: Andrew Plant, Winnersh (GB); Thomas Geller, Odenthal (DE); Bernd Gallenkamp, Wuppertal (DE); Rolf Grosser, Leverkusen (DE); Albrecht Marhold, Leverkusen (DE); Christoph Erdelen, Leichlingen (DE); Andreas Turberg, Haan (DE); Olaf Hansen, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 216 days.

This patent is subject to a terminal disclaimer.

(21) Appl. No.: 10/380,433

(22) PCT Filed: Sep. 10, 2001

(86) PCT No.: PCT/EP01/10424

§ 371 (c)(1),
(2), (4) Date: Jul. 28, 2003

(87) PCT Pub. No.: WO02/24643

PCT Pub. Date: Mar. 28, 2002

(65) Prior Publication Data

US 2004/0059129 A1 Mar. 25, 2004

(30) Foreign Application Priority Data

Sep. 22, 2000 (DE) ................. 100 47 110

(51) Int. Cl.
*A01N 55/08* (2006.01)
*A01N 43/36* (2006.01)
*A61K 31/40* (2006.01)
*C07D 207/00* (2006.01)
*C07D 207/18* (2006.01)

(52) U.S. Cl. ................. 504/193; 504/283; 514/428; 514/429; 548/405; 548/565

(58) Field of Classification Search ................. 548/405, 548/565; 514/428, 429; 504/193, 283
See application file for complete search history.

(56) References Cited

U.S. PATENT DOCUMENTS

| | | | |
|---|---|---|---|
| 5,274,167 A | 12/1993 | Lange et al. | 560/40 |
| 5,945,413 A | 8/1999 | Tung et al. | 514/193 |
| 6,162,417 A | 12/2000 | Goodman et al. | 424/1.85 |
| 6,274,613 B1 * | 8/2001 | Plant et al. | 514/408 |
| 6,399,771 B1 * | 6/2002 | Plant et al. | 540/611 |
| 6,489,490 B1 * | 12/2002 | Plant et al. | 548/525 |
| 6,599,924 B1 | 7/2003 | Plant et al. | 514/343 |
| 6,632,833 B1 * | 10/2003 | Plant et al. | 514/422 |
| 6,770,595 B2 * | 8/2004 | Plant et al. | 504/218 |
| 2004/0054194 A1 * | 3/2004 | Plant et al. | 548/577 |
| 2004/0082586 A1 * | 4/2004 | Plant et al. | 514/252.05 |
| 2004/0147764 A1 * | 7/2004 | Kraatz et al. | 548/577 |

FOREIGN PATENT DOCUMENTS

| | | |
|---|---|---|
| WO | 94/29268 | 12/1994 |
| WO | 98/22438 | 5/1998 |
| WO | 99/59967 | 11/1999 |
| WO | 99/59968 | 11/1999 |

OTHER PUBLICATIONS

Tombo et al., Chirality and Corp Protection, Angewandte Chemie, 30(10), (1991), pp. 1193-1386.*
Official Journal EPO, May 1990, pp. 195-212, decision T 296/87, (1990).*
Tetrahedron Letters, vol. 38, No. 22, pp. 3841-3844, (month unavailable) 1997, "One Pot Biaryl Synthesis via in situ Boranate Formation" by A. Giroux et al.
J. Med. Chem., (month unavailable) 1996, 39, pp. 4396-4405, "Synthesis Activity, and Molecular Modeling of New Series of Tricyclic Pyridazinones as Selective Aldose Reductase Inhibitors" by L. Costantino et al.
J. Org. Chem., (month unavailable) 1996, 61, pp. 5813-5817, "Asymmetric Synthesis of *Cis*- Fused Bicyclic Pyrrolidines and Pyrrolidinones via Chiral Polycyclic Lactams" by M. D. Ennis et al.
Tetrahedron Letters 39, (month unavailable) 1998, pp. 2705-2706, "A Novel Protecting Group for Hindered Phenois" by M. M. Hansen et al.
Tetrahedron Letters, vol. 34, No. 51, pp. 8237-8240, (month unavailable) 1993, "Synthesis of Extended Chromogenic Tetra-(p-substituted-phenyl)-tetraethoxycalix[4]arenes" by M. S. Wong et al.
Chem. Pharm. Bull., 36(6), pp. 2050-2060, (month unavailable) 1988, "Studies on Antiheumatic Agents: 3-Benzoylpropionic Acid Derivatives" by K. Kameo et al.

(Continued)

*Primary Examiner*—Rebecca L Anderson
(74) *Attorney, Agent, or Firm*—Richard E. L. Henderson

(57) ABSTRACT

Novel optically active $\Delta^1$-pyrrolines of the formula (I)

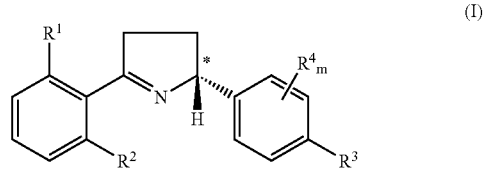

in which
$R^1$, $R^2$, $R^3$, $R^4$, and m are each as defined in the description, a plurality of the processes for preparing these substances and their use for controlling pests.

2 Claims, No Drawings

OTHER PUBLICATIONS

Org. Prep. Proced. Int., 27, (month unavailable) 1995, pp. 550-552, "An Improved Synthesis of Fenbufen" by R. Castillo et al.

J. Org. Chem., (month unavailable) 1995, 60, pp. 7508-7510, "Palladium(0)-Catalyzed Cross-Coupling Reaction of Alkoxydiboron with Haloarenes: A Direct Procedure for Arylboronic Esters" by T. Ishiyama et al.

Tetrahedron: Asymmetry, vol. 7, No. 6, pp. 1835-1843, (month unavailable) 1996, "Stereocontrolled Synthesis of Chiral Secondary (α-methylene-β-Substituted)-γ-Lactams by Addition of β-Functional Crotylzinc Reagents to Chiral Imines" by V. Nyzam et al.

J. Org Chem., (month unavailable) 1992, 57, pp. 1656-1662, "A Simple Asymmetric Synthesis of 2-Substituted Pyrrolidines and 5-Substituted Pyrrolidinones" by L. E. Burgess et al.

Synthetic Communications, 18(10), pp. 1159-1165, (month unavailable) 1988, "Reaction of Oxiranes with Dianions of Secondary Amides. New Entry to 5-Alkylsubstituted γ-Lactams" by H. Takahata et al.

Methoden Der Organischen Chemie [Method of Organic Chemistry] 4th ed., vol. III, Chapter 6, (month unavailable) 1952, pp. 635-638, "III. Thermische Umwandlungen von Carbonsäureestern". by H. Henecka.

Synthetic Communications, 26(21), pp. 3897-3901, (month unavailable) 1996, "A General And Versatile Synthesis of 4- And 5-Oxoacids" by G. Lhommet et al.

Heterocycles, vol. 44, No. 1, (month unavailable) 1997, pp. 213-225, "Practical Synthesis of (S)-3-(p-Nitrobenzyloxycarbonylamino)Pyrrolidine and Its Related Compounds From L-Aspartic Acid" by H. Tomori et al.

Protective Groups In Organic Synthesis, 3rd Edition, (month unavailable) 1999, pp. 520-525, "Protection for the Amino Group" by T. W. Green et al.

Angew. Chem., 37, (month unavailable) 1998, pp. 1987-2021, (English trans) for Angew Chen, 1998, 110, "Reduction of Carbonyl Compounds with Chiral Oxazaborolidine Catalysts: A New Paradigm for Enantioselective Catalysis and a Powerful New Synthetic Method" by E. J. Corey et al.

\* cited by examiner

OPTICALLY ACTIVE 2,5-BISARYL-Δ¹-PYRROLINES AND THEIR USE AS PEST CONTROL AGENTS

The present patent application has been filed under 35 U.S.C. 371 as a national stage application of PCT/EP01/10424, filed Sep. 10, 2001, which was published in German as International Patent Publication WO 02/24643 on Mar. 28, 2002, and is entitled to the right of priority of German Patent Application 100 47 110.2, filed Sep. 22, 2000.

The invention relates to novel optically active 2,5-bisaryl-Δ¹-pyrrolines, processes for their preparation and to their use as pesticides.

Racemic Δ¹-pyrroline pesticides have already been described in WO00/21958, WO 99/59968, WO 99/59967 and WO 98/22438.

However, the efficacy and/or duration of action of these prior-art racemates is, in particular against certain organisms and/or at low application rates, not entirely satisfactory in all areas of use.

Owing to the multifarious requirements that modem pesticides have to meet, for example with respect to efficacy, duration of action, activity spectrum, use spectrum, toxicity, combination with other active compounds, combination with formulation auxiliaries or synthesis, and owing to the possible occurrence of resistance, however, the development of such substances can never be considered as being concluded, and there is always a great need for novel compounds which, at least in some aspects, offer advantages over the known compounds.

It is an object of the present invention to provide optically active compounds of the general formula (I). When used as pesticides, these compounds allow the application rates to be reduced.

The present invention provides novel optically active Δ¹-pyrrolines of the formula (I)

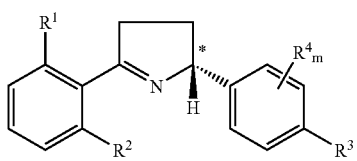

(I)

in which
* represents a chiral carbon atom having the (R)-configuration,
m represents 0, 1, 2, 3 or 4,
$R^1$ represents halogen or methyl,
$R^2$ represents hydrogen or halogen,
$R^3$ represents hydrogen, halogen, hydroxyl, alkyl, alkenyl, alkinyl, halogenoalkyl, halogenoalkenyl, alkoxy, —S(O)$_o$R$^6$, —OSO$_2$R$^6$, bisalkoxyborane, —B(OH)$_2$ or represents phenyl which is optionally mono- or polysubstituted by radicals from the list $W^1$,
$R^4$ represents halogen, alkyl, alkoxy, halogenoalkyl, halogenoalkoxy or —S(O)$_o$R$^6$,
$W^1$ represents cyano, halogen, hydroxyl, alkyl, alkoxy, halogenoalkyl, halogenoalkoxy, alkenyl, halogenoalkenyl, alkenyloxy, halogenoalkenyloxy, alkoxycarbonyl, trialkylsilyl, trialkylsilyloxy, —CONH$_2$, —NR$^7$R$^8$, —S(O)$_o$R$^6$ or —SO$_2$NR$^7$R$^8$,
o represents 0, 1 or 2,
$R^6$ represents hydrogen, alkyl or halogenoalkyl,
$R^7$ and $R^8$ independently of one another each represent hydrogen, alkyl, halogenoalkyl or together represent alkylene or alkoxyalkylene.

In the formulae of all the compounds described above and below, an asterisk (*) denotes in each case a chiral carbon atom with (R)-configuration.

Moreover, it has been found that optically active compounds of the formula (I) are obtained when
A) racemic compounds of the formula (I-rac)

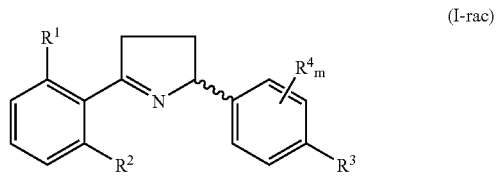

(I-rac)

in which
$R^1$, $R^2$, $R^3$, $R^4$ and m are each as defined above,
are chromatographed on a stationary chiral silica gel phase in the presence of an eluent or an eluent mixture as liquid phase, or
B) (i) compounds of the formula (I-a)

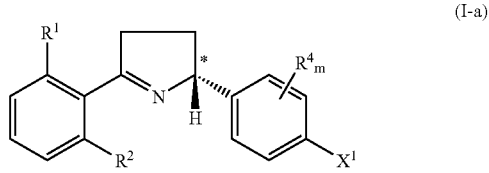

(I-a)

in which
$R^1$, $R^2$, $R^4$ and m are each as defined above and
$X^1$ represents Cl, Br, I, —OSO$_2$CF$_3$, —OSO$_2$(CF$_2$)$_3$CF$_3$,
are reacted with organometallic compounds of the formula (II)

A-M (II)

in which
A represents phenyl which is optionally mono- or polysubstituted by radicals from the list $W^1$,
where $W^1$ is as defined above and
M represents —B(OH)$_2$, Sn("Bu)$_3$ or ZnCl,
M furthermore represents MgCl,
in the presence of a catalyst, if appropriate in the presence of an acid binder and if appropriate in the presence of a diluent, or
(ii) compounds of the formula (I-b)

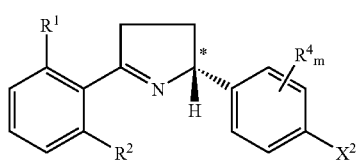

(I-b)

in which
$R^1$, $R^2$, $R^4$ and m are each as defined above,
$X^2$ represents —B(OH)$_2$, (4,4,5,5-tetramethyl-1,3,2-dioxoborolan)-2-yl, (5,5-dimethyl-1,3,2-dioxoborinan)-2- yl, (4,4,6-trimethyl-1,3,2-dioxoborinan)-2-yl, 1,3,2-benzodioxaborol-2-yl, Sn("Bu)$_3$ or ZnCl, are reacted with aromatic compounds of the formula (III)

$$T-A \qquad (III)$$

in which

A represents phenyl which is optionally mono- or polysubstituted by radicals from the list $W^1$, where $W^1$ is as defined above, and T represents Cl, Br, I, —OSO$_2$CF$_3$, —OSO$_2$(CF$_2$)$_3$CF$_3$, in the presence of a catalyst, if appropriate in the presence of an acid binder and if appropriate in the presence of a diluent, or (iii) compounds of the formula (I-a)

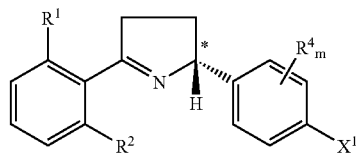

(I-a)

in which $R^1$, $R^2$, $R^4$, $X^1$ and m are each as defined above, are reacted in a tandem reaction with aromatic compounds of the formula (III)

$$T-A \qquad (III)$$

in which

A and T are each as defined above, in the presence of a catalyst, in the presence of 4,4,4',4',5,5,5',5'-octamethyl-2,2'-bis-1,3,2-dioxaborolane or of 5,5,5',5'-tetramethyl-2,2'-bis-1,3,2-dioxaborinane or of 4,4,4',4',6,6'-hexamethyl-2,2'-bis-1,3,2-dioxaborinane or of 2,2'-bis-1,3,2-benzodioxaborole and, if appropriate, in the presence of an acid binder and, if appropriate, in the presence of a diluent, or C) optically active aminoketones of the formula (IV)

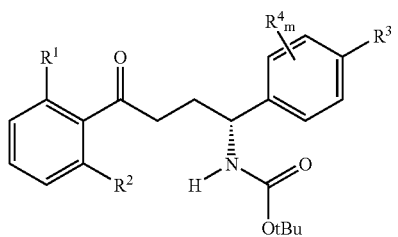

(IV)

in which $R^1$, $R^2$, $R^3$, $R^4$ and m are each as defined above, are deprotected by treatment with a Lewis acid or protic acid and the amine that is formed in situ is cyclized in the presence of an acid.

Finally, it has been found that the compounds of the formula (I) according to the invention have very good insecticidal properties and can be used both in crop protection and in the protection of materials for controlling undesirable pests such as insects.

Surprisingly, the compounds of the formula (I) according to the invention have considerably better insecticidal activity than the known racemates, which are likewise known to be highly active compounds having insecticidal properties, and than the (S)-configured analogues.

Surprisingly, the column material for separating the racemic compounds of the formula (I-rac) used in process (A), which was selected from a large number of commercially available solid phases tested, is the only material that affords the corresponding enantiomers in high purity and with high yield.

The formula (I) provides a general definition of the compounds according to the invention. Preferred substituents or ranges of the radicals listed under the formulae mentioned above and below are illustrated below.

m preferably represents 0, 1, 2 or 3.

$R^1$ preferably represents fluorine, chlorine, bromine or methyl.

$R^2$ preferably represents hydrogen, fluorine, chlorine or bromine.

$R^3$ preferably represents hydrogen, fluorine, chlorine, bromine, iodine, hydroxyl, $C_1$-$C_6$-alkyl, $C_2$-$C_6$-alkenyl, $C_2$-$C_6$-alkinyl, $C_1$-$C_6$-halogenoalkyl, $C_2$-$C_6$-halogenoalkenyl, $C_1$-$C_6$-alkoxy, —S(O)$_o$R$^6$, —OSO$_2$R$^6$, bis($C_4$-$C_8$-alkoxy)borane, —B(OH)$_2$ or represents phenyl which is optionally mono- or polysubstituted by radicals from the list $W^1$.

$R^4$ preferably represents halogen, $C_1$-$C_6$-alkyl, $C_1$-$C_6$-alkoxy, $C_1$-$C_6$-halogenoalkyl, $C_1$-$C_6$-halogenoalkoxy or —S(O)$_o$R$^6$.

$W^1$ preferably represents cyano, halogen, hydroxyl, $C_1$-$C_6$-alkyl, $C_1$-$C_6$-alkoxy, $C_1$-$C_6$-halogenoalkyl, $C_1$-$C_6$-halogenoalkoxy, $C_2$-$C_6$-halogenoalkenyloxy, $C_1$-$C_6$-alkoxycarbonyl, tri($C_1$-$C_4$-alkyl)silyl, tri($C_1$-$C_4$-alkyl)silyloxy, —S(O)$_o$R$^6$ or —SO$_2$NR$^7$R$^8$.

o preferably represents 0, 1 or 2.

$R^6$ preferably represents hydrogen, $C_1$-$C_6$-alkyl or $C_1$-$C_6$-halogenoalkyl.

$R^7$ and $R^8$ independently of one another each preferably represent hydrogen, $C_1$-$C_6$-alkyl, $C_1$-$C_6$-halogenoalkyl or together represent $C_2$-$C_6$-alkylene or $C_1$-$C_4$-alkoxy-$C_1$-$C_4$-alkylene (for example morpholine).

m particularly preferably represents 0, 1, or 2.

$R^1$ particularly preferably represents fluorine, chlorine or methyl.

$R^2$ particularly preferably represents hydrogen, fluorine or chlorine.

$R^3$ particularly preferably represents hydrogen, fluorine, chlorine, bromine, hydroxyl, $C_1$-$C_6$-alkyl, $C_2$-$C_6$-alkenyl, $C_2$-$C_6$-alkinyl, $C_1$-$C_6$-alkoxy; represents in each case fluorine- or chlorine-substituted $C_1$-$C_6$-alkyl or $C_2$-$C_6$-alkenyl; represents —S(O)$_o$R$^6$, —OSO$_2$R$^6$, (5,5-dimethyl-1,3,2-dioxoborinan)-2-yl, (4,4,5,5-tetramethyl-1,3,2-dioxoborolan)-2-yl, (4,4,6-trimethyl-1,3,2-dioxoborinan)-2-yl, 1,3,2-benzodioxaborol-2-yl, —B(OH)$_2$ or represents phenyl which is optionally mono- to trisubstituted by radicals from the list $W^1$.

$R^4$ particularly preferably represents fluorine, chlorine, bromine, $C_1$-$C_6$-alkyl, $C_1$-$C_6$-alkoxy, in each case fluorine- or chlorine-substituted $C_1$-$C_6$-alkyl or $C_1$-$C_6$-alkoxy or represents —S(O)$_o$R$^6$. p0 $W^1$ particularly preferably represents cyano, fluorine, chlorine, bromine, iodine, hydroxyl, $C_1$-$C_4$-alkyl, $C_1$-$C_4$-alkoxy, in each case fluorine- or chlorine-substituted $C_1$-$C_4$-alkyl, $C_1$-$C_4$-alkoxy, $C_2$-$C_6$-alkenyloxy, represents $C_1$-$C_4$-alkoxycarbonyl, —OSi(Me$_2$)t-Bu, —S(O)$_o$R$^6$ or —SO$_2$NR$^7$R$^8$.

o particularly preferably represents 0, 1, or 2.

$R^6$ particularly preferably represents hydrogen, $C_1$-$C_6$-alkyl or represents fluorine- or chlorine-substituted $C_1$-$C_4$-alkyl.

$R^7$ and $R^8$ independently of one another each particularly preferably represent hydrogen, $C_1$-$C_6$-alkyl, fluorine- or chlorine-substituted $C_1$-$C_6$-alkyl, or together represent $C_4$-$C_5$-alkylene.

m very particularly preferably represents 0, 1 or 2.

$R^1$ very particularly preferably represents fluorine, chlorine or methyl.

$R^2$ very particularly preferably represents hydrogen, fluorine or chlorine.

$R^3$ very particularly preferably represents hydrogen, chlorine, bromine, hydroxyl, methyl, ethyl, n-propyl, isopropyl, n-butyl, isobutyl, sec-butyl, tert-butyl, 2-propenyl, butenyl, propargyl, butinyl, methoxy, ethoxy, n-propoxy, n-butoxy, isobutoxy, sec-butoxy, tert-butoxy, —$SO_2CF_3$, —$SO_2(CF_2)_3CF_3$, —$OSO_2CF_3$, —$OSO_2(CF_2)_3CF_3$, (5,5-dimethyl-1,3,2-dioxoborinan)-2-yl, (4,4,5,5-tetramethyl-1,3,2-dioxoborolan)-2-yl, (4,4,6-trimethyl-1,3,2-dioxoborinan)-2-yl, 1,3,2-benzodioxaborol-2-yl, —$B(OH)_2$ or represents fluorine- or chlorine-substituted $C_1$-$C_4$-alkyl or represents phenyl which is optionally mono- to trisubstituted by radicals from the list $W^1$.

$R^3$ furthermore very particularly preferably represents isopropoxy.

$R^4$ very particularly preferably represents fluorine, chlorine, bromine, methyl, ethyl, methoxy, ethoxy, trifluoromethyl, difluoromethoxy, trifluoromethoxy or —$SO_2CF_3$.

$W^1$ furthermore very particularly preferably represents cyano, fluorine, chlorine, bromine, hydroxyl, methyl, ethyl, n-propyl, isopropyl, n-butyl, isobutyl, sec-butyl, tert-butyl, methoxy, ethoxy, n-propoxy, n-butoxy, isobutoxy, sec-butoxy, tert-butoxy, trifluoromethoxy, difluoromethoxy, —$CF_3$, —$CHF_2$, —$CClF_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, —$OCF_2CF_2H$, —$OCF=CF_2$, —$SCF_3$, —$SOCF_3$, —$SO_2CF_3$, —$SCHF_2$, —$SOCHF_2$, —$SO_2CHF_2$, —$OSi(Me_2)t$-Bu, —$SO_2NMe_2$ or —$CO_2Et$.

$W^1$ furthermore very particularly preferably represents isopropoxy.

Preference is furthermore given to compounds of the formulae (I-c), (I-d), (I-e), (I-f) and (I-g)

(I-c)

(I-d)

(I-e)

(I-f)

(I-g)

in which in each case
$R^3$ is as defined above and
$R^{4-1}$ represents hydrogen, methoxy or ethoxy.

Preference is furthermore given to compounds of the formulae (I-h), (I-i), (I-j), (I-k) and (I-l)

(I-h)

(I-i)

(I-j)

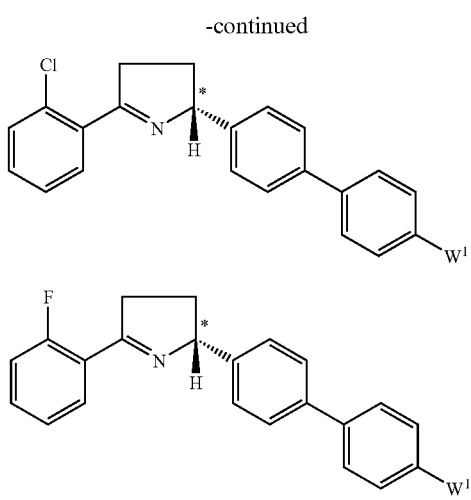

in which in each case
W¹ is as defined above.

In the definitions mentioned above, oxyalkylene and thioalkylene represent —O-alkyl- and —S-alkyl-, respectively, and alkyleneoxy and alkylenethio represent -alkyl-O— and -alkyl-S—, respectively, oxyalkyleneoxy represents —O-alkyl-O—.

Preference, particular preference and very particular preference is given to compounds which carry the substituents mentioned above as being preferred, particularly preferred and very particularly preferred, respectively.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can be mono- or polysubstituted, where in the case of polysubstitution the substituents can be identical or different. A plurality of radicals having the same indices, such as, for example, m radicals $R^4$ for m>1, can be identical or different.

However, the abovementioned general or preferred radical definitions or illustrations can also be combined with one another as desired, i.e. including combinations between the respective ranges and preferred ranges. They apply to the end products and also, correspondingly, to the precursors and intermediates.

Illustration of the Processes and Intermediates:

Process A

The formula (I-rac) provides a general definition of the racemic compounds required as starting materials for carrying out the Process A according to the invention. In this formula, $R^1$, $R^2$, $R^3$, $R^4$ and m each preferably, particularly preferably and very particularly preferably have those meanings which have already been mentioned in connection with the description of the compounds of the formula (I) according to the invention as being preferred, particularly preferred etc. for these radicals.

The racemic compounds of the formula (I-rac) used for carrying out the Process A according to the invention are known and can be prepared by known processes (WO 00/21958, WO 99/59968, WO 99/59967 and WO 98/22438).

When carrying out the Process A according to the invention, methods of preparative chromatography, preferably the High Performance Liquid Chromatography (HPLC) method, are employed. For this purpose, a chiral stationary silica gel phase is used. A silica gel modified by tris(3,5-dimethylphenylcarbamate)-cellulose has been found to be particularly suitable for separating the compounds of the formula (I-rac) into the two enantiomers. This separation material is commercially available. However, it is also possible to use other stationary phases as chromatography material.

Process B

Using (2R)-5-(2,6-difluorophenyl)-2-(4-trifluoromethylsulphonyloxyphenyl)-3,4-dihydro-2H-pyrrole, 4-trifluoromethoxyphenylboronic acid and a palladium catalyst as starting materials, the Process B(i) according to the invention can be illustrated by the equation below.

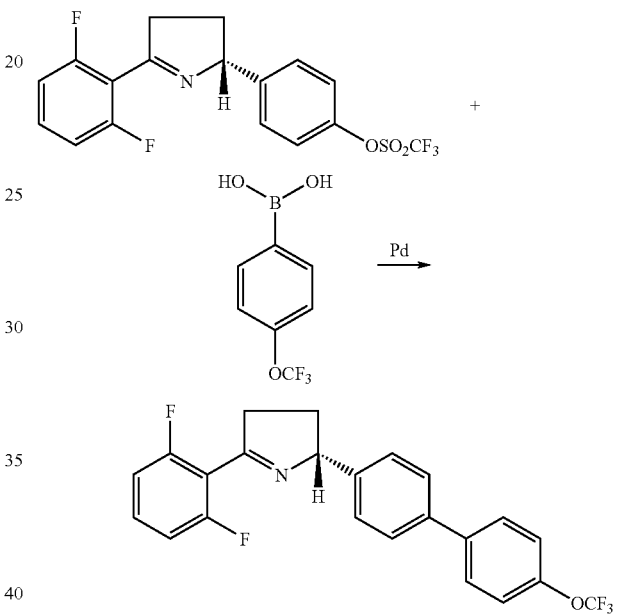

Using (2R)-5-(2,6-difluorophenyl)-2-[4-(4,4,5,5-tetramethyl-1,3,2-dioxaborolan-2-yl)phenyl]-3,4-dihydro-2H-pyrrole, 4-trifluoromethoxy-bromophenyl and a palladium catalyst, the Process B(ii) according to the invention can be illustated by the equation below.

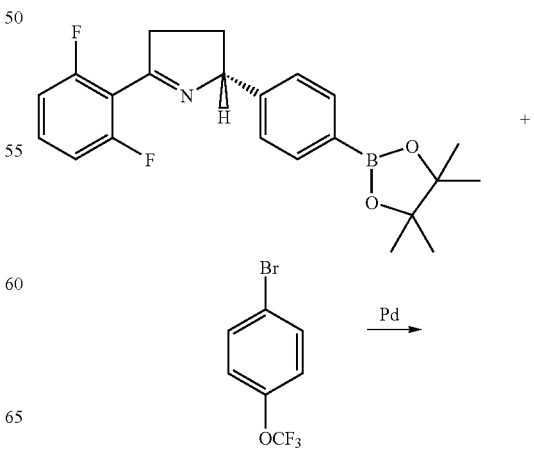

-continued

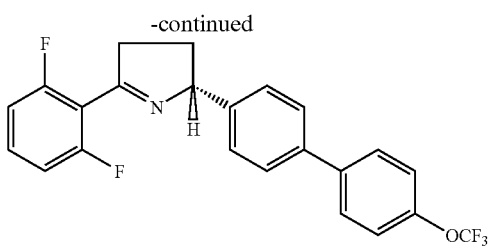

Using (2R)-5-(2,6-difluorophenyl)-2-(4-bromo-phenyl)-3,4-dihydro-2H-pyrrole, 4-trifluoromethoxy-bromophenyl, a palladium catalyst and 4,4,4',4',5,5,5',5'-octamethyl-2,2'-bis-1,3,2-dioxaborolane as starting materials, the Process B(iii) according to the invention can be illustrated by the equation below.

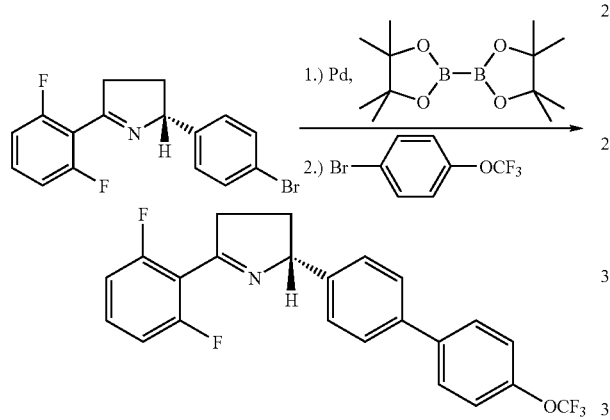

The formulae (I-a) and (I-b) provide a general definition of the compounds required as starting materials for carrying out the Process B according to the invention. In these formulae, $R^1$, $R^2$, $R^4$ and m each preferably, particularly preferably and very particularly preferably have those meanings which have already been mentioned in connection with the description of the compounds of the formula (I) according to the invention as being preferred, particularly preferred etc. for these radicals.

$X^1$ preferably represents Cl, Br, —OSO$_2$CF$_3$ or —OSO$_2$(CF$_2$)$_3$CF$_3$.

$X^1$ particularly preferably represents Cl, Br or —OSO$_2$CF$_3$.

$X^1$ very particularly preferably represents Cl, Br or —OSO$_2$CF$_3$.

$X^2$ preferably represents —B(OH)$_2$, (4,4,5,5-tetramethyl-1,3,2-dioxoborolan)-2-yl, (5,5-dimethyl-1,3,2-dioxoborinan)-2-yl, (4,4,6-trimethyl-1,3,2-dioxoborinan)-2-yl, 1,3,2-benzodioxaborol-2-yl, Sn("Bu)$_3$ or ZnCl.

$X^2$ particularly preferably represents —B(OH)$_2$, (4,4,5,5-tetramethyl-1,3,2-dioxoborolan)-2-yl, (5,5-dimethyl-1,3,2-dioxoborinan)-2-yl, (4,4,6-trimethyl-1,3,2-dioxoborinan)-2-yl or 1,3,2-benzodioxaborol-2-yl.

$X^2$ very particularly preferably represents —B(OH)$_2$, (4,4,5,5-tetramethyl-1,3,2-dioxoborolan)-2-yl or (4,4,6-trimethyl-1,3,2-dioxoborinan)-2-yl.

Here, the radicals $R^6$, $R^7$ and $R^8$ each preferably, particularly preferably and very particularly preferably have those meanings which have already been mentioned in connection with the description of the compounds of the formula (I) according to the invention as being preferred, particularly preferred etc. for these radicals.

Optically active cyclic imines of the formulae (I-a) and (I-b) are novel and are prepared analogously to Process A or C.

The formula (II) provides a general definition of the organometallic compounds required as starting materials for carrying out the Process B(i) according to the invention.

A preferably represents phenyl which is unsubstituted or mono- to tetrasubstituted by radicals from the list W$^1$.

A particularly preferably represents phenyl which is unsubstituted or mono- or disubstituted by radicals from the list W$^1$.

A very particularly preferably represents phenyl which is mono- or disubstituted by radicals from the list W$^1$.

Here, W$^1$ preferably, particularly preferably and very particularly preferably has those meanings which have already been mentioned in connection with the description of the compounds of the formula (I) according to the invention as being preferred, particularly preferred etc. for these radicals.

M preferably represents —B(OH)$_2$, Sn("Bu)$_3$ or ZnCl.

M furthermore preferably represents MgCl.

M particularly preferably represents —B(OH)$_2$ or Sn("Bu)$_3$.

M very particularly preferably represents —B(OH)$_2$.

Some of the organometallic compounds of the formula (II) are known. However, boronic acids [for example in the case where M=—B(OH)$_2$], for example, can also be prepared from (bromo)aromatics by lithiation or Br—Li (Mg) exchange and subsequent reaction with tris-alkoxyboron compounds (cf., for example, Tetrahedron Lett. 1993, 34, 8237-8240).

The formula (III) provides a general definition of the aromatics required as starting materials for carrying out the Processes B(ii) and B(iii) according to the invention. Here A preferably, particularly preferably and very particularly preferably represents those radicals which have already been mentioned in the description of the compounds of the formula (II) as being preferred, particularly preferred and very particularly preferred, respectively.

T preferably represents Cl, Br, —OSO$_2$CF$_3$ or —OSO$_2$(CF$_2$)$_3$CF$_3$.

T particularly preferably represents Cl, Br or —OSO$_2$CF$_3$.

T very particularly preferably represents Br or —OSO$_2$CF$_3$.

Aromatics of the formula (III) are generally known and/or commercially available.

The Process B(iii) according to the invention can be carried out in two variants. It is possible to initially charge either a compound of the formula (I-a) or a compound of the formula (III). Process B(iii) can be considered to be a tandem reaction of Processes B(i) and B(ii).

When carrying out the Process B according to the invention, a palladium catalyst is generally used which for its part can be used with or without addition of further ligands. The catalyst used is preferably PdCl$_2$(dppf) [dppf=1,1'-bis(diphenylphosphino)ferrocene], Pd(PPh$_3$)$_4$, PdCl$_2$(PPh$_3$)$_2$, PdCl$_2$(CH$_3$CN)$_2$, Pd$_2$(dba)$_3$ [dba=dibenzylideneacetone] or Pd(OAc)$_2$, particularly preferably PdCl$_2$(dppf), Pd(PPh$_3$)$_4$, PdCl$_2$(PPh$_3$)$_2$, or Pd(OAc)$_2$, very particularly preferably PdCl$_2$(dppf) or Pd(PPh$_3$)$_4$.

When carrying out the Process B(i) according to the invention, most preference is given to using PdCl$_2$(dppf), Pd(PPh$_3$)$_4$ or Pd(OAc)$_2$.

When carrying out the Process B(ii) according to the invention, most preference is given to using Pd$_2$(dba)$_3$.

When carrying out the Process B(iii) according to the invention, most preference is given to using PdCl$_2$(dppf) in the first step and PdCl$_2$(dppf), Pd(PPh$_3$)$_4$ or Pd(OAc)$_2$ in the second step of the tandem reaction.

Suitable ligands are triarylphosphines, trialkylphosphines or arsines. Preference is given to using dppf, PPh$_3$, P(t-Bu)$_3$, Pcy$_3$ or AsPh$_3$, particularly preferably dppf.

Starting with compounds of the formula (I-b) [X$^2$=(4,4,5,5-tetramethyl-1,3,2-dioxoborolan)-2-yl], it is also possible to prepare compounds of the formula (I) analogously to known methods (J. Org. Chem. 1995, 60, 7508; Tetrahedron Lett. 1997, 38, 3841).

Process C

Using tert-butyl (1R)-4-(2,6-difluorophenyl)-4-oxo-1-[4'-(trifluoromethoxy)-1,1'-biphenyl-4-yl]butylcarbamate and trifluoroacetic acid as starting materials, the course of the Process C according to the invention can be illustrated by the equation below.

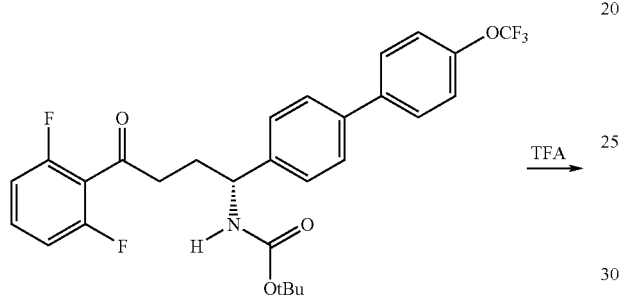

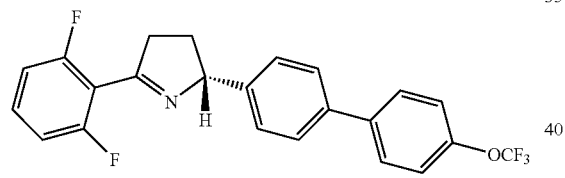

The formula (IV) provides a general definition of the aminoketones required as starting materials for carrying out the Process C according to the invention. In this formula, R$^1$, R$^2$, R$^3$, R$^4$ and m each preferably, particularly preferably and very particularly preferably have those meanings which have already been mentioned in connection with the description of the compounds of the formula (I) according to the invention as being preferred, particularly preferred etc. for these radicals.

Optically active aminoketones of the formula (IV)

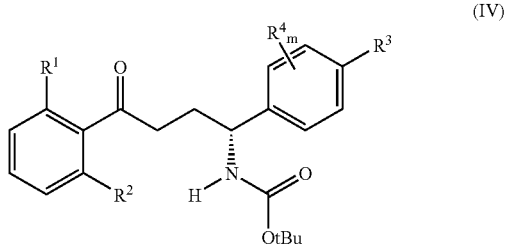

in which

R$^1$, R$^2$, R$^3$, R$^4$ and m are each as defined above, are novel. They can be prepared by α) reacting optically active N-Boc-lactams of the formula (V)

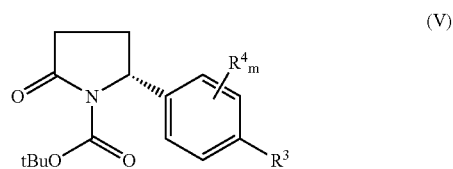

in which

R$^3$, R$^4$ and m are each as defined above, with metallated aromatics of the formula (VI)

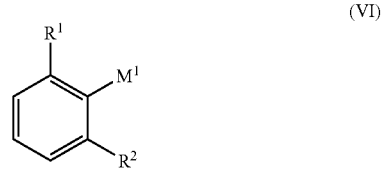

in which

R$^1$ and R$^2$ are each as defined above and

M$^1$ represents Li, MgCl, MgBr, MgI, ZnCl, in the presence of a diluent at temperatures between −70° C. and +70° C.

The formula (VI) provides a general definition of the metallated aromatics required as starting materials for carrying out the Process α. In this formula, R$^1$ and R$^2$ preferably, particularly preferably and very particularly preferably have those meanings which have already been mentioned in connection with the description of the compounds of the formula (I) according to the invention as being preferred, particularly preferred etc. for these radicals. M$^1$ preferably represents Li, MgCl, MgBr, MgI, ZnCl, particularly preferably Li, MgCl, MgBr, MgI, very particularly preferably Li, MgCl, MgBr.

Some of the metallated aromatics of the formula (VI) are known, or they can be prepared by known methods, such as, for example, lithiation or Grignard reaction, from the corresponding aromatics or halogenated aromatics.

The formula (V) provides a general definition of the N-Boc-lactams required as starting materials for carrying out the Process α. In this formula, R$^3$, R$^4$ and m each preferably, particularly preferably and very particularly preferably have those meanings which have already been mentioned in connection with the description of the compounds of the formula (I) according to the invention as being preferred, particularly preferred etc. for these radicals.

N-Boc-lactams of the formula (V) are novel. They can be prepared, for example, by β) reacting optically active lactams of the formula (VII)

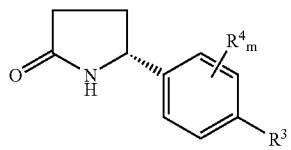

(VII)

in which

R³, R⁴ and m are each as defined above, by customary methods for example with di-tert-butyl dicarbonate in the presence of a base (cf. Tetrahedron Lett. 1998, 39, 2705-2706).

The formula (VII) provides a general definition of the lactams required as starting materials for carrying out the Process β. In this formula, R³, R⁴ and m each preferably, particularly preferably and very particularly preferably have those meanings which have already been mentioned in connection with the description of the compounds of the formula (I) according to the invention as being preferred, particularly preferred etc. for these radicals.

Optically active lactams of the formula (VII) are novel. They can be prepared by γ) chromatographing racemic lactams of the formula (VII-rac)

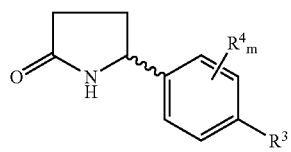

(VII-rac)

in which

R³, R⁴ and m are each as defined above, on a chiral stationary silica gel phase and concentrating the eluate under reduced pressure, or by δ) reacting γ-ketocarboxylic acids of the formula (VIII)

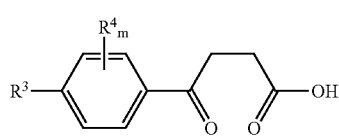

(VIII)

in which

R³, R⁴ and m are each as defined above, in a multi-step synthesis, or by

ε) reacting γ-ketocarboxylic acid esters of the formula (VIII-a)

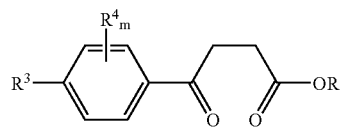

(VIII-a)

in which

R represents alkyl and

R³, R⁴ and m are each as defined above, in a multi-step synthesis.

The formula (VII-rac) provides a general definition of the racemic lactams required as starting materials for carrying out the Process γ. In this formula, R³, R⁴ and m each preferably, particularly preferably and very particularly preferably have those meanings which have already been mentioned in connection with the compounds of the formula (I) according to the invention as being preferred, particularly preferred etc. for these radicals.

Racemic lactams of the formula (VII-rac) are known and can be prepared by known processes (WO 99/59968, WO 99/59967 and WO 98/22438).

When carrying out the Process γ, methods of preparative chromatography, preferably the High Performance Liquid Chromatography (HPLC) method, are employed. Here, a chiral stationary silica gel phase is used. A silica gel derivative (for example mercaptopropyl silica gel) modified with N-methacryloyl-L-leucin-D-menthylamide has been found to be particularly suitable for separating the compounds of the formula (VII-rac) (cf. EP-A 0 379 917).

Surprisingly, the racemic lactams of the formula (VII-rac) can be separated on a kg scale in a short period of time (gradients shorter than 20 min) by repeated chromatography on relatively short columns [450 mm×75 mm, (I.D.)], this process thus also being suitable for industrial use. Compared to commercial stationary chiral phases, the material used has considerably higher enantioselectivity values α (α=16 as compared to α=3 to 4; the higher the α value, the better the separation of the enantiomers).

The multi-step Process δ according to the invention can be illustrated by the equation below.

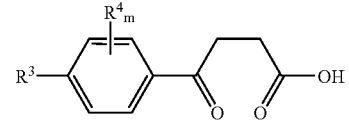

(VIII)

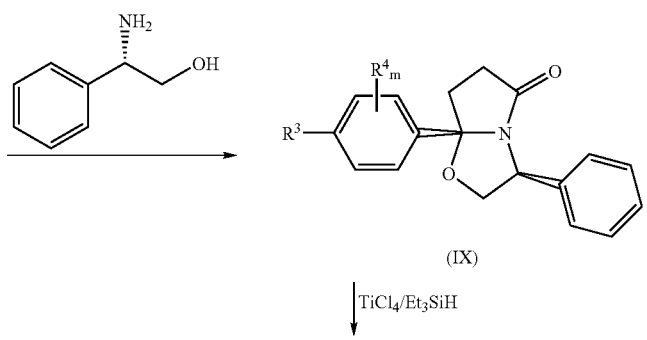

(IX)

↓ TiCl₄/Et₃SiH

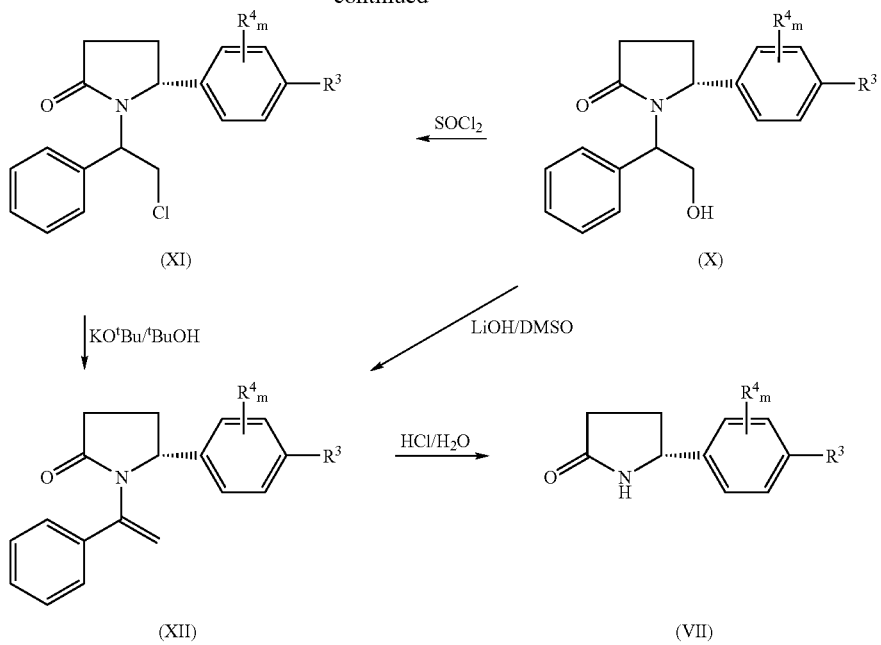

γ-Ketocarboxylic acids of the formula (VIII) are condensed with 2(S)-2-amino-2-phenylethanol to give bicyclic lactams of the formula (IX) which are predominantly obtained as one diastereomer.

Reductive cleavage of bicyclic lactams of the formula (IX) using a Lewis acid (for example $TiCl_4$) and a reducing agent (for example $Et_3SiH$) gives N-protected γ-lactams of the formula (X) (cf. J. Org. Chem. 1992, 57, 1656).

The hydroxyl group in γ-lactams of the formula (X) can be converted into a leaving group (in particular a chlorine atom, cf. Tetrahedron Asymmetry 1996, 7, 1835) using a chlorinating agent (for example thionyl chloride), giving chlorides of the formula (XI).

Dehydrohalogenation of (XI) by treatment with a base (for example KOtBu) gives N-vinyllactams of the formula (XII).

It is also possible to convert γ-lactams of the formula (X) directly, for example by treatment with a base (for example LiOH) in a suitable solvent (for example DMSO) at temperatures between 60° C. and 140° C. into the N-vinyllactams of the formula (XII) (cf. J. Org. Chem. 1996, 61, 5813).

Acid-promoted hydrolysis of (XII) (using, for example, 1 M HCl) gives γ-lactams of the formula (VII) (cf. J. Org. Chem. 1996, 61, 5813).

The formula (VIII) and the formulae (IX), (X), (XI) and (XII) provide general definitions of the γ-ketocarboxylic acids required as starting materials for carrying out the Process δ according to the invention and the intermediates, respectively. In these formulae, $R^3$, $R^4$ and m each preferably, particularly preferably and very particularly preferably have those meanings which have already been mentioned in connection with the description of the compounds of the formula (I) according to the invention as being preferred, particularly preferred etc. for these radicals.

Some of the γ-ketocarboxylic acids of the formula (VIII) are known. Some of the methods by which they can be prepared are known. γ-Ketocarboxylic acids of the formula (VIII) are obtained, for example, by reacting appropriate aromatics with succinic anhydride or succinic acid monoester chloride in the presence of a Lewis acid (for example aluminium chloride) and, if appropriate, in the presence of a diluent (for example 1,2-dichlorethane) (cf., for example, Org. Prep. Proced. Int. 1995, 27, 550-552).

In the case of aromatics which do not permit a Friedel-Crafts acylation, it is alternatively possible to use a corresponding organometallic derivative, such as, for example, a Grignard reagent (cf. Syn. Commun. 1996, 26, 3897).

It is also possible to prepare γ-ketocarboxylic acids of the formula (VIII) by reducing α,β-unsaturated carbonyl compounds of the formula (XIII) using, for example, Zn dust in glacial acetic acid according to the reaction scheme below (cf. Chem. Pharm. Bull. 1988, 36, 2050).

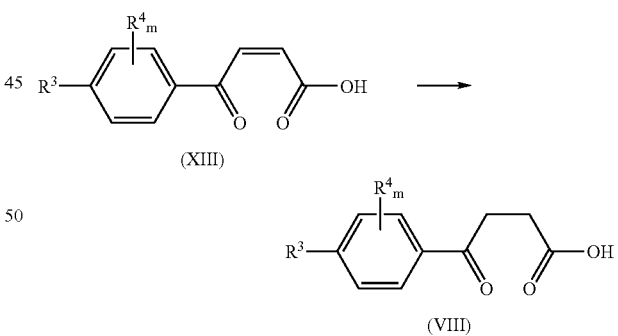

The formula (XIII) provides a general definition of the carbonyl compounds. In this formula, $R^3$, $R^4$ and m each preferably, particularly preferably and very particularly preferably have those meanings which have already been mentioned in connection with the description of the compounds of the formula (I) according to the invention as being preferred, particularly preferred etc. for these radicals.

Some of the α,β-unsaturated carbonyl compounds of the formula (XIII) are known, and/or they can be prepared, for example, by condensing acetophenones of the formula (XIV) with glyoxalic acid in the presence of a base (for example NaOH) and, if appropriate, in the presence of a diluent (for example water, EtOH) according to the reaction scheme below (cf., for example, J. Med. Chem. 1996, 39, 4396).

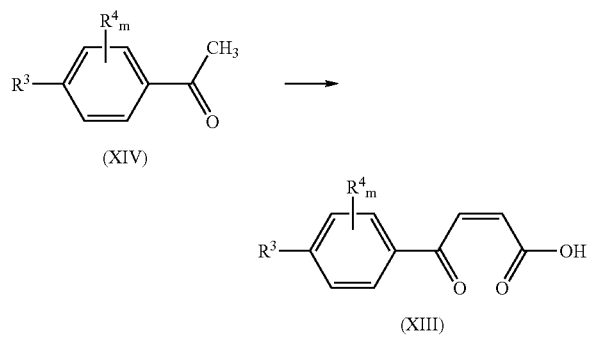

The formula (XIV) provides a general definition of the acetophenones. In this formula, $R^3$, $R^4$ and m each preferably, particularly preferably and very particularly preferably have those meanings which have already been mentioned in connection with the description of the compounds of the formula (I) according to the invention as being preferred, particularly preferred etc. for these radicals. Acetophenones of the formula (XIV) are known.

The multi-step Process ε can be illustrated by the equation below.

The reaction of a γ-ketocarboxylic ester of the formula (VIII-a) with allylamine in the presence of ammonium chloride gives allylamides of the formula (XV) (cf. Houben-Weyl, Methoden der Organischen Chemie [Methods of Organic Chemistry], 4th Edition, Volume VIII, Chapter 6, p. 653 ff.).

According to the Corey, Bakshi & Shibata protocol (CBS reduction), the ketofunctionality in compounds of the formula (XV) can be enantioselectively reduced in the presence of a catalyst {for example (3aR)-1-methyl-3,3,6-triphenyltetrahydro-3H-pyrrolo[1,2-c][1,3,2]oxazaborol, commercially available} (cf. Angew. Chem. 1998, 110, 2093 and references cited therein).

The subsequent cyclization of compounds of the formula (XVI) to give N-allyllactams of the formula (XVII) can be carried out by double-deprotonation with KOtBu and reaction with tosyl chloride (cf. Synth. Commun. 1988, 18, 1159), without noticeable loss of stereochemical information. In contrast to the literature reference, it is surprisingly possible to dispense with the use of the carcinogenic hexamethylphosphoric triamide (HMPT) cosolvent.

The allyl protective group is removed in an aqueous THF solution in the presence of toluenesulphonic acid with the addition of 10 mol % of Pd(Ph$_3$P)$_4$ (cf. Heterocycles 1997, 44, 213 and references cited therein), giving the lactam of the formula (VII). The desired enantiomer can be enriched by recrystallization from petroleum ether (40/60)/toluene.

The formula (VIII-a) and the formulae (XV), (XVI) and (XVII) provide general definitions of the γ-ketocarboxylic

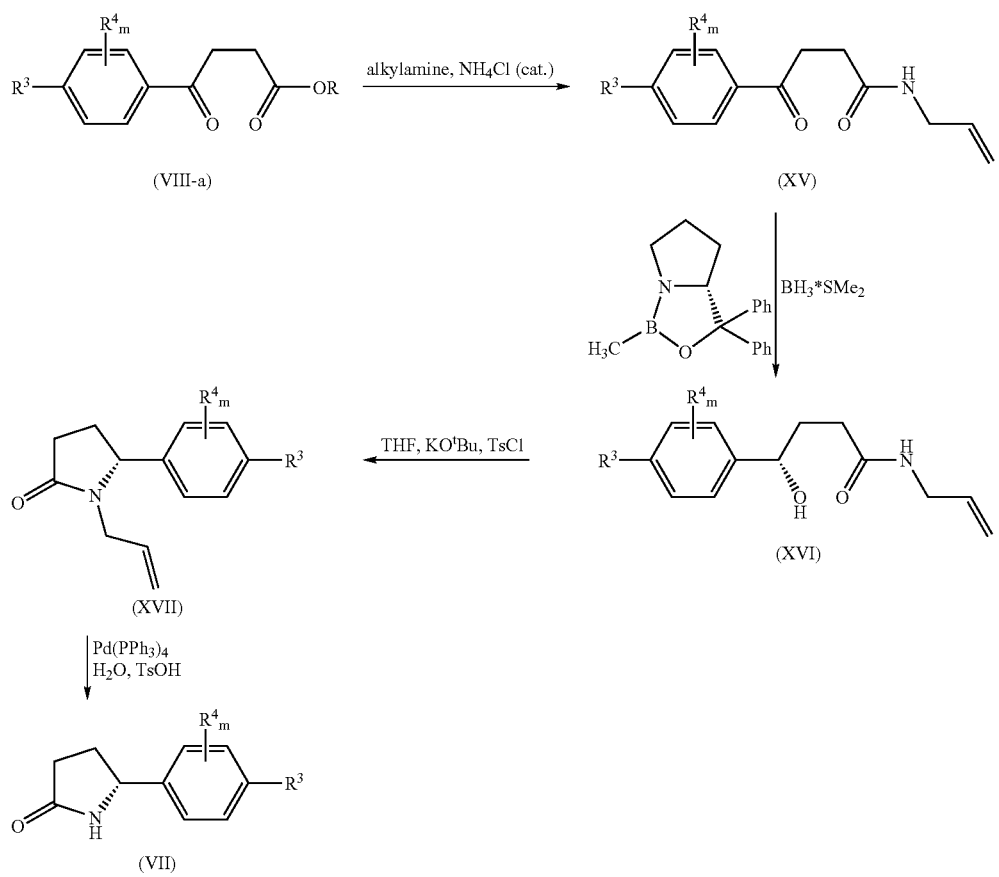

esters required as starting materials for carrying out the Process ϵ according to the invention and the intermediates, respectively. In these formulae, $R^3$, $R^4$ and m each preferably, particularly preferably and very particularly preferably have those meanings which have already been mentioned in connection with the description of the compounds of the formula (I) according to the invention as being preferred, particularly preferred etc. for these radicals.

γ-Ketocarboxylic esters of the formula (VIII-a) can be prepared from the corresponding acids of the formula (VIII) by known esterification processes.

Suitable acid binders for carrying out the Process B according to the invention are in each case all of the inorganic and organic bases customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkali metal fluorides, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to carry out the process without additional acid binder or to use an excess of the amine component so that it simultaneously acts as acid binder. Particular preference is given to using barium hydroxide, tripotassium phosphate, caesium carbonate, potassium carbonate, sodium carbonate, potassium acetate, triethylamine, KOtBu, caesium fluoride or potassium fluoride.

Suitable diluents for carrying out the Processes B and C according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl-t-butyl ether, methyl-t-amyl ether, dioxane, tetrahydrofuran, 1,2-dimethoxyethane, 1,2-diethoxyethahe or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

Suitable eluents for carrying out the Process A according to the invention are in each case all customary inert organic solvents and also mixtures of these. Preference is given to using optionally halogenated aliphatic, alicyclic or aromatic hydrocarbons, such as petroleum ether, hexane, heptane, cyclohexane; dichloromethane, chloroform; alcohols, such as methanol, ethanol, propanol; nitriles, such as acetonitrile; esters, such as methyl acetate or ethyl acetate. Particular preference is given to using aliphatic hydrocarbons, such as hexane or heptane, and alcohols, such as methanol or propanol, very particularly preferably n-heptane and isopropanol or mixtures of these.

Suitable diluents for carrying out the Process B according to the invention are, particularly preferably, acetone, dimethoxyethane, dioxane, THF, DMF, dimethylacetamide, DMSO, ethanol, toluene or, if appropriate, mixtures of the diluents mentioned with water.

Suitable diluents for carrying out the Process C according to the invention are, particularly preferably, methylene chloride, chloroform, toluene, methanol or ethanol.

Suitable acids for carrying out the Process C according to the invention are in each case all customary Lewis acids or protic acids. Methods for removing Boc are generally known (cf., for example, T. W. Greene, P. G. M. Wuts, Protective Groups in Organic Synthesis, Ed. 3, New York, Wiley & Sons, 1999, pp. 520-525). Preference is given to using trifluoroacetic acid, HCl or HBr for removing the Boc protective group.

When carrying out the Process A according to the invention, the reaction temperatures can in each case be varied within a relatively wide range. In general, the process is carried out at temperatures between 10° C. and 60° C., preferably between 10° C. and 40° C., particularly preferably at room temperature.

When carrying out the Process B according to the invention, the reaction temperatures can in each case be varied within a relatively wide range. In general, the process is carried out at temperatures between 0° C. and 140° C., preferably between 10° C. and 120° C., particularly preferably between 20° C. and 120° C.

When carrying out the Process C according to the invention, the reaction temperatures can in each case be varied within a relatively wide range. In general, the process is carried out at temperatures between −20° C. and +120° C., preferably between −10° C., and 60° C.

When carrying out the Process A according to the invention, in general an about 1% strength solution of the racemic compound (I-rac) is used for the chromatographic separation. However, it is also possible to use other concentrations. Work-up is carried out by customary methods. In general, the eluate is substantially concentrated and solid components are filtered off and, after washing with n-heptane, dried. The residue is, if appropriate, freed chromatographically of any impurities that may still be present. For this purpose, the eluents used are mixtures of n-hexane or cyclohexane and ethyl acetate, the composition of which has to be adapted to the compound to be purified in each case.

When carrying out the Process B(i) according to the invention, in general 1 mol or a slight excess of organometallic compound of the formula (II) is employed per mole of the compound of the formula (I-a). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. If required, the residue is freed by customary methods such as chromatography or recrystallization from any impurities that may still be present.

When carrying out the Process B(ii) according to the invention, in general 1 mol or a slight excess of aromatic of the formula (III) is employed per mole of the compound of the formula (I-b). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. If required, the residue is freed by customary methods such as chromatography or recrystallization from any impurities that may still be present.

When carrying out the Process B(iii) according to the invention, in general 1 mol or a slight excess of a diboron compound and 1 mol or a slight excess of a (hetero)aromatic of the formula (III) and 3% of a palladium catalyst are employed per mole of the compound of the formula (I-a). However, it is also possible to employ the reaction components in other ratios. It is optionally possible initially to charge the compound of the formula (I-a) or the compound of the formula (III). Work-up is carried out by customary methods. In general, the reaction mixture is diluted with water and extracted with ethyl acetate. The organic phase is washed with water, dried over sodium sulphate, filtered and concentrated. If required, the residue is freed by customary methods such as chromatography or recrystallization from any impurities that may still be present.

When carrying out the Process C according to the invention, in general 100 mol of a protic acid are employed per mole of the compound of the formula (IV). However, it is also possible to employ the reaction components in other ratios. Work-up is carried out by customary methods. In general, the reaction mixture is concentrated, taken up in a suitable solvent and adjusted to pH 12 using sodium hydroxide, and the organic phase is washed with water, dried over sodium sulphate, filtered and concentrated. If required, the residue is freed by customary methods such as chromatography or recrystallization from any impurities that may still be present.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera Vastatrix , Pemphigus* spp., *Macrosiphum avenae, Myzus* spp., *Phorodon humuli, Rhopalosiphum padi , Empoasca* spp., *Euscelis bilobatus, Nephotettix cincticeps,* *Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica Dermestes* spp., *Trogoderma.* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp.,*Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

In particular, the compounds of the formula (I) according to the invention have excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montrnorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks;

as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates;

as dispersants there are suitable: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, as a mixture with other, also known active compounds, such as insecticides, attractants, sterilizing agents, bactericides, acaricides, nematicides, fungicides, growth-regulating substances or herbicides, in order, in this way, for example, to broaden the spectrum of activity or to prevent the development of resistance. In many cases, synergistic effects are obtained, i.e. the activity of the mixture exceeds the activity of the individual components. The insecticides include, for example, phosphoric acid esters, carbamates, carboxylates, chlorinated hydrocarbons, phenylureas and substances produced by microorganisms, inter alia.

Suitable co-components are, for example, the following compounds:

Fungicides:

aldimorph, ampropylfos, ampropylfos-potassium, andoprim, anilazine, azaconazole, Azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazirn, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbarn, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, firmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-yclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl[(4-chlorophenyl)-azo]-cyanoacetate, potassium bicarbonate, methanetetrathiol-sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis(2-propinyloxy)-phenyl]-N'-methoxy-methanimidamide, N-formyl-N-hydroxy-DL-alanine-sodium salt, O,O-diethyl[2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyran-2,1'(3'H)-isobenzofuran]-3'-one, 4-[3,4-dimethoxyphenyl)-3-(4-fluorophenyl)-acryloyl]-morpholine.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetarniprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethruin, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiarnethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, Verticillium lecanii,

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyryridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate, N-cyanomethyl-4-trifluoromethyl-nicotinamide 3,5-dichloro-1-(3,3-dichloro-2-propenyloxy)-4-[3-(5-trifluoromethylpyridin-2-yloxy)-propoxy]-benzene.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenetic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") which have been obtained by conventional breeding, by mutagenesis or by genetic engineering. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and corresponding expressed proteins and toxins. Traits that are furthermore particularly emphasized are the increased tolerance of the plants to certain herbicidally active compounds, for example imidazolinones, sulphonylureas, glyphosates or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the formula (I) and/or the active compound mixtures according to the invention. The preferred ranges stated above for the active compounds and/or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks such as, for example, *Amblyomma hebraeum*, and against parasitic flies such as, for example, *Lucilia cuprina*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina*.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-comarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing agents.

Particularly effective preservation of wood is achieved by impregnation processes on a large industrial scale, for example vacuum, double vacuum or pressure processes. The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyoluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Omithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicularidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The preparation and use of the substances according to the invention are illustrated by the examples below.

PREPARATION EXAMPLES

Processs A

Racemate Resolution: $\Delta^1$-Pyrrolines of the Formula (I)

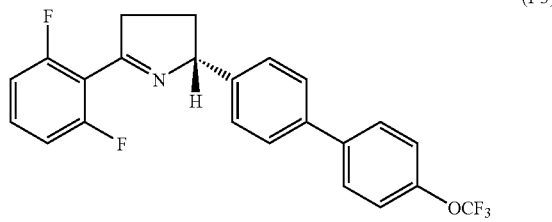

(I-3)

(+/−)-5-(2,6-Difluorophenyl)-2-[4'-(trifluoromethoxy)-1,1'-biphenyl-4-yl]-3,4-dihydro-2H-pyrrole (I-3) (8 g) is dissolved in 1 l of n-heptane/isopropanol 9:1 (v/v=volume/volume). The solution is then fractionally chromatographed on the silica gel phase Chiralcel OD® [manufacturer: Daicel (Japan), column dimensions: 500 mm×40 mm (I.D.), particle size: 20 μm, flow rate: 40 ml/min] by High Performance Liquid Chromatography using the mobile phase n-heptane/isopropanol 9:1 (v/v). To resolve the total amount, every 30 min 5 ml (corresponding in each case to 40 mg of the racemate) are applied to the column. The compounds are detected using a UV detector, at a wavelength of 254 nm. Following analysis for enantiomeric purity, the appropriate eluate fractions are pooled and substantially concentrated under reduced pressure and the residues are filtered off and, after washing with n-heptane, dried. The resulting crude product is purified on silica gel (mobile phase: n-hexane/ethyl acetate, 1:9→1:4, in each case v/v).

This gives 7 g of (2R)-5-(2,6-difluorophenyl)-2-[4'-(trifluoromethoxy)-1,1'-biphenyl-4-yl]-3,4-dihydro-2H-pyrrole (I-3).

The following optically active $\Delta^1$-pyrrolines of the formula (I) are obtained by Process A:

| No. | Structure | Optical rotation $[\alpha]_D$ | ee value |
|---|---|---|---|
| I-1 | 2-CH$_3$-phenyl / pyrroline / biphenyl-OCF$_3$ | +44.07 (c = 0.91, CH$_3$CN); 23° C. | 99.4% |
| I-2 | 2-Cl-phenyl / pyrroline / biphenyl-OCF$_3$ | +2.80 (c = 1.0, MeOH); 20° C. | 99.7% |
| I-3 | 2,6-F$_2$-phenyl / pyrroline / biphenyl-OCF$_3$ | +7.70 (c = 1.5, CHCl$_3$); 20° C. | 99.5% |
| I-4 | 2,6-F$_2$-phenyl / pyrroline / biphenyl-SCF$_3$ | +31.29 (c = 0.62, MeOH); 20° C. | 99.5% |
| I-5 | 2,6-F$_2$-phenyl / pyrroline / biphenyl-OCF$_2$CF$_2$H | +36.7 (c = 1.0, MeOH); 20° C. | 99.0% |

-continued

| No. | Structure | Optical rotation [α]_D | ee value |
|---|---|---|---|
| I-6 | 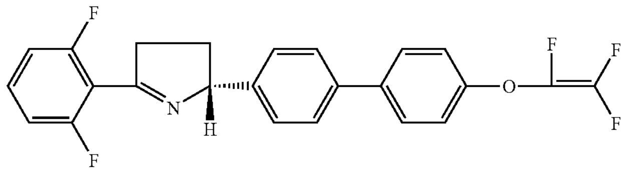 | +32.2 (c = 1.1, MeOH); 20° C. | 99.6% |
| I-7 | 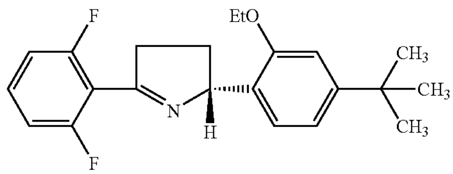 | +45.9 (c = 0.30, CHCl₃); 20° C. | 99.4% |

Process B: Palladium-Catalysed Coupling Reactions

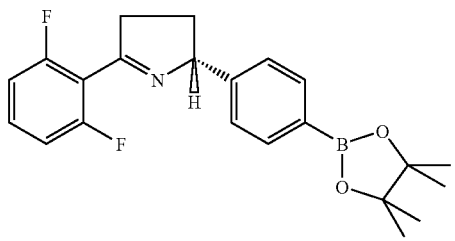
(I-b-1)

4-[(2R)-5-(2,6-Difluorophenyl)-3,4-dihydro-2H-pyrrole-2-yl]phenyl trifluoromethanesulphonate (I-a-1) (1.01 g, 2.5 mmol), bis(pinacolato)diboron (0.76 g, 3.0 mmol), KOAc (0.74 g, 7.5 mmol), PdCl$_2$[dppf] (60 mg, 0.075 mmol) and dimethoxyethane (15 ml) are stirred under an atmosphere of argon at 80° C. for 3.5 h. The reaction mixture is cooled to room temperature, diluted with water and extracted with ethyl acetate. The organic phase is washed with brine, dried over sodium sulphate, filtered and concentrated under reduced pressure. The residue that remains is taken up in dichloromethane, 5 g of Florisil are added and the solution is concentrated. The crude product is purified chromatographically on silica gel (mobile phase: cyclohexane/ethyl acetate, 4:1 v/v).

This gives 0.55 g (57% of theory) of (2R)-5-(2,6-difluorophenyl)-2-[4-(4,4,5,5-tetramethyl-1,3,2-dioxaborolan-2-yl)phenyl]-3,4-dihydro-2H-pyrrole (I-b-1).

HPLC: log P (pH 7)=4.47 (purity 96.6%);
Optical rotation: [α]$_D$=+24.8 (c=0.9, MeOH); 20° C.

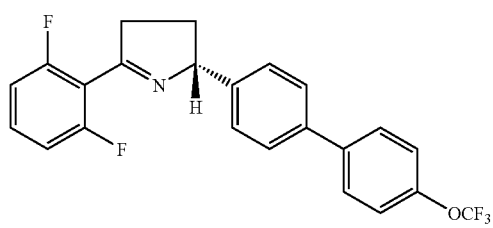
(I-3)

4-[(2R)-5-(2,6-Difluorophenyl)-3,4-dihydro-2H-pyrrol-2-yl]phenyl trifluoromethanesulphonate (I-a-1) (1.01 g, 2.5 mmol), bis(pinacolato)diboron (0.76 g, 3.0 mmol), KOAc (0.74 g, 7.5 mmol), PdCl$_2$[dppf] (60 mg, 0.075 mmol) and dimethoxyethane (15 ml) are stirred at 80° C. for 3 h. The reaction mixture is cooled to room temperature. 4-Trifluoromethoxyphenylbromobenzene (III-1) (0.72 g, 3 mmol), PdCl$_2$[dppf] (60 mg, 0.075 mmol) and 2 M aqueous Na$_2$CO$_3$ solution (7.5 ml) are then added, and the mixture is stirred at 80° C. for 16 h. The reaction mixture is cooled to room temperature, diluted with water and extracted with ethyl acetate. The organic phase is washed with water, dried over sodium sulphate and filtered. Florisil (4 g) is added and the solution is concentrated under reduced pressure. The crude product is purified chromatographically on silica gel (mobile phase: n-hexane/ethyl acetate, 1:9→1:4, in each case v/v).

This gives 0.61 g (59% of theory) of (2R)-5-(2,6-difluorophenyl)-2-[4'-(trifluoromethoxy)-1,1'-biphenyl-4-yl]-3,4-dihydro-2H-pyrrole (I-3).

HPLC: log P (pH 2.3)=4.08 (purity 94.4%);
Optical rotation: [α]$_D$=+33.9 (c=0.9, MeOH); 20° C.

(I-11)

4-[(2R)-5-(2,6-Difluorophenyl)-3,4-dihydro-2H-pyrrol-2-yl]phenyl trifluoromethanesulphonate (I-a-1) (1.01 g, 2.5 mmol), bis(neopentylglycolato)diboron (0.68 g, 3.0 mmol), KOAc (0.74 g, 7.5 mmol), PdCl$_2$[dppf] (60 mg, 0.075 mmol) and N,N-dimethylacetamide (15 ml) are stirred at 80° C. for 3 h. The reaction mixture is cooled to room temperature. 4-Bromophenyl trifluoromethyl sulphone (III-11) (0.72 g, 3 mmol), PdCl$_2$[dppf] (60 mg, 0.075 mmol) and 2 M aqueous Na$_2$CO$_3$ solution (7.5 ml) are then added and the mixture is stirred at 80° C. for 16 h. The reaction mixture is cooled to room temperature, diluted with water and extracted with ethyl acetate. The organic phase is washed with water, dried over sodium sulphate and filtered. Florisil (4 g) is added and the solution is concentrated under reduced pressure. The crude product is purified chromatographically on silica gel (mobile phase: n-hexane/ethyl acetate, 4:1, v/v).

This gives 0.60 g (52% of theory) of (2R)-5-(2,6-difluorophenyl)-2-{4'-[(trifluoromethyl)sulphonyl]-1,1'-biphenyl-4-yl}-3,4-dihydro-2H-pyrrole (I-11).

HPLC: log P (pH 2.3)=3.92 (purity 100%);

Optical rotation: $[\alpha]_D$=+36.0 (c=0.35, methanol); 20° C.

4-[(2R)-5-(2,6-Difluorophenyl)-3,4-dihydro-2H-pyrrol-2-yl]phenyl trifluoromethanesulphonate (I-a-1) (9.00 g, 22.2 mmol), 4-{[tert-butyl(dimethyl)silyl]oxy}phenylboronic acid (II-1) (8.40 g, 33.3 mmol), $K_2CO_3$ (6.14 g, 44.4 mmol), Pd[PPh$_3$]$_4$ (1.28 g, 1.1 mmol), dimethoxyethane (150 ml), and distilled water (50 ml) are stirred at 80° C. overnight. The reaction mixture is cooled to room temperature and taken up in ethyl acetate (300 ml). The organic phase is washed with water, dried over sodium sulphate, filtered and concentrated under reduced pressure. The crude products are purified by silica gel chromatography (mobile phase: toluene/ethyl acetate, 4:1 v/v).

This gives 7.67 g (75% of theory) of (2R)-2-(4'-{[tert-butyl(dimethyl)silyl]oxy}-1,1'-biphenyl-4-yl)-5-(2,6-difluorophenyl)-3,4-dihydro-2H-pyrrole (1-8) of melting point 33° C.

HPLC: log P (pH 2.3)=6.20 (purity 93.68%).

This gives 1.80 g (23% of theory) of 4'-[(2R)-5-(2,6-difluorophenyl)-3,4-dihydro-2H-pyrrol-2-yl]-1,1'-biphenyl-4'-ol (I-9) of melting point 217° C.

HPLC: log P (pH 2.3)=1.93 (purity 98.48%).

The following further optically active $\Delta^1$-pyrrolines of the formula (I) are obtained by Process B:

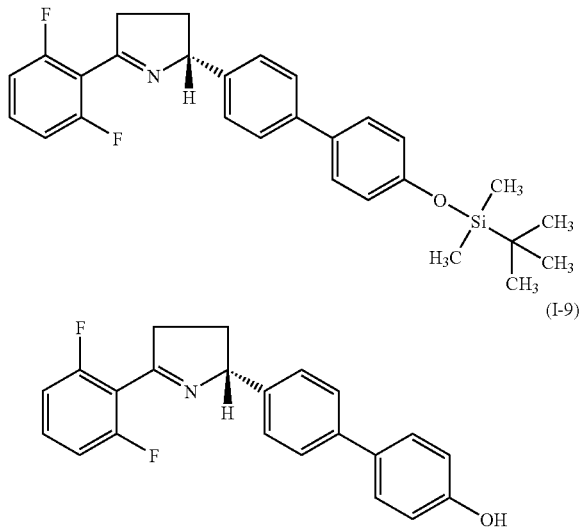

| No. | Structure | Optical rotation $[\alpha]_D$ | log p/m.p. |
|---|---|---|---|
| I-10 | 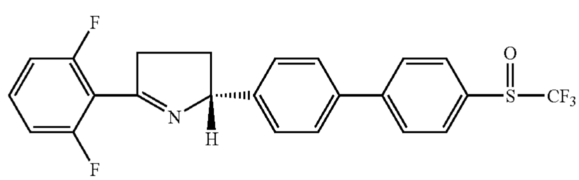 | | m.p. 146–148° C. |
| I-11 | 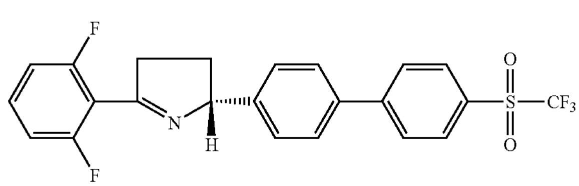 | +36.0 (c = 0.35, MeOH); 20° C. | log P 3.92 |
| I-12 | 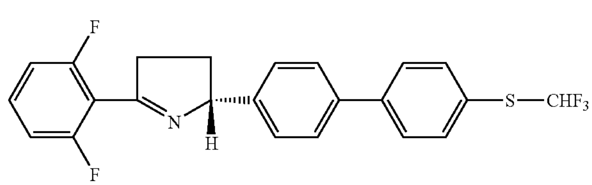 | | |

| No. | Structure | Optical rotation [α]$_D$ | log p/m.p. |
|---|---|---|---|
| I-13 | 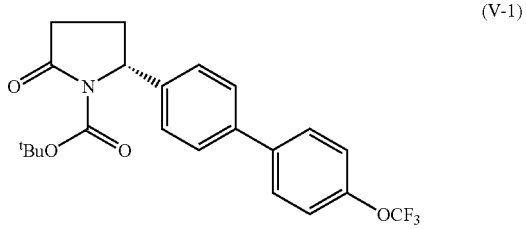 | | |
| I-14 | 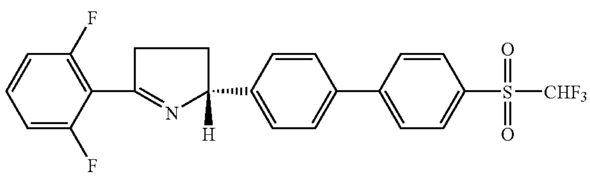 | | m.p. 148–150° C. |

Process C

Conversion of Laclams of the Formula (VII) Into N-Boc-Lactams of the Formula (V)

(V-1)

(5R)-5-[4'-(Trifluoromethoxy)-1,1'-biphenyl-4-yl]-2-pyrrolidinone (VII-1) (0.51 g, 77.9% pure, about 1.23 mmol) is initially charged in dichloromethane (10 ml). t-Butoxycarbonyl anhydride (1.9 mmol, 0.56 g) and dimethylaminopyridine (0.02 g, 0.32 mmol) are added, and the reaction mixture is stirred at room-temperature overnight. The mixture is diluted with dichloromethane (40 ml) and the organic phase is washed successively with 1 M HCl, saturated: aqueous sodium bicarbonate solution and brine, dried over magnesium sulphate, filtered and concentrated under reduced pressure.

This gives 0.42 g (75% of theory) of tert-butyl (5R)-2-oxo-5-[4'-(trifluoromethoxy)-1,1'-biphenyl-4-yl]-1-pyrrolidine carboxylate (V-1), which is reacted further as crude product without additional purification.

HPLC: log P (pH 2.3)=4.32 (purity 93.1%).

(V-2)

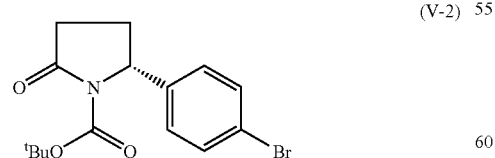

(5R)-5-(4-Bromophenyl)-2-pyrrolidinone (VII-2) (1.38 g, 5.7 mmol) is initially charged in dichloromethane (40 ml). tert-Butoxycarbonyl anhydride (6.9 mmol, 1.50 g) and dimethylaminopyridine (0.14 g, 1.14 mmol) are added, and the reaction mixture is stirred at room temperature for two days.

The organic phase is washed successively with 1 M HCl, saturated aqueous sodium bicarbonate solution and brine, dried over magnesium sulphate, filtered and concentrated under reduced pressure. The crude product is stirred with isopropanol and filtered off with suction.

This gives 0.71 g (35% of theory) of tert-butyl (2R)-2-(4-bromophenyl)-5-oxo-1-pyrrolidinecarboxylate (V-2).

HPLC: log P (pH 2.3)=3.04 (purity 96.5%).

The following compounds are synthesized analogously:

| No. | Structure | log P (pH 2.3) |
|---|---|---|
| V-3 | 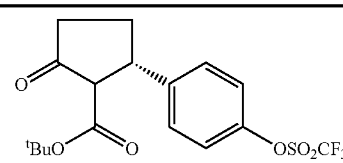 | 3.31 |
| V-4 | 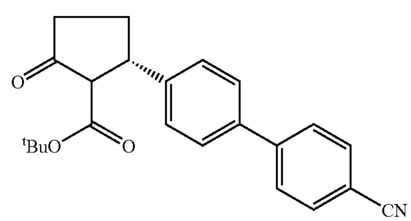 | 3.02 |

Conversion of N-Boc-Lactams of the Formula (V) in to N-Boc-Aminoketones of the Formula (IV)

(IV-1)

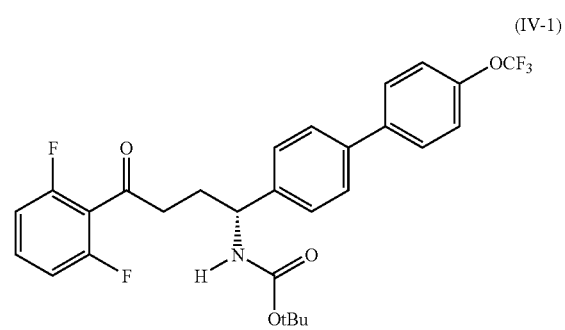

Under an atmosphere of argon, 1,3-difluorobenzene (0.29 g, 2.55 mmol) is, at −78° C., initially charged in THF (30 ml). n-BuLi (1.6 M in hexane, 2.55 mmol, 1.59 ml) and tetram-ethylethylenediamine (2.55 mmol, 0.38 ml) are successively added dropwise to this solution. The mixture is stirred at −78° C. for 20 min, and compound (V-1) (1.70 mmol, 0.72 g) in THF (2 ml) is then added at this temperature. The reaction mixture is allowed to warm to room temperature overnight and then poured into water (10 ml). The aqueous phase is extracted with ethyl acetate (100 ml) and the organic phase is washed with brine, dried over magnesium sulphate, filtered and concentrated under reduced pressure.

This gives 0.52 g (30% of theory) of tert-butyl (1R)-4-(2,6-difluorophenyl)-4-oxo-1-[4'-(trifluoromethoxy)-1,1'-biphenyl-4-yl]butylcarbamate (IV-1), which is reacted further as crude product without additional purification.

HPLC: log P (pH 2.3)=5.18 (purity 52.9%).

(IV-2)

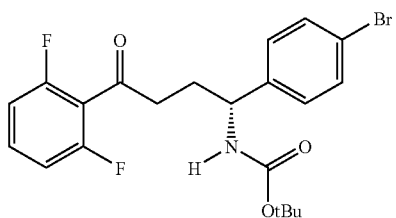

Under an atmosphere of argon, 1,3-difluorobenzene (0.31 g, 2.7 mmol) is, at −78° C., initially charged in THF (20 ml). n-BuLi (1.6 M in hexane, 2.7 mmol, 1.69 ml) is added dropwise to this solution. The mixture is stirred at −78° C. for 15 min, and compound V-2 (1.80 mmol, 0.60 g) in THF (2 ml) is then added dropwise at this temperature. The reaction mixture is allowed to warm to room temperature overnight and then poured into water (10 ml). The aqueous phase is extracted with ethyl acetate (100 ml) and the organic phase is washed with brine, dried over magnesium sulphate, filtered and concentrated under reduced pressure.

This gives 0.65 g (60% of theory) of tert-butyl (1R)-1-(4-bromophenyl)-4-(,6-difluorophenyl)-4-oxobutylcarbamate (IV-2), which is reacted further as crude product without additional purification.

HPLC: log P (pH 2.3)=4.22 (purity 75.3%).

The following compounds are synthesized analogously:

| No. | Structure | log P (pH 2.3) |
|---|---|---|
| IV-3 | 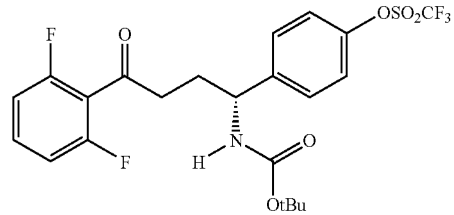 | 4.37 |
| IV-4 | 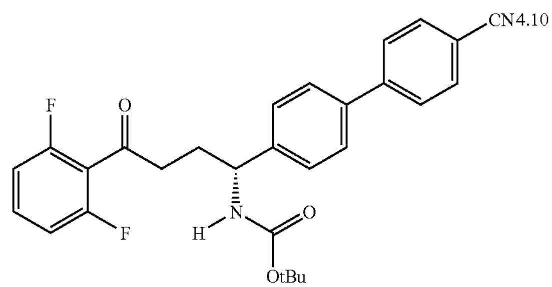 | 4.10 |

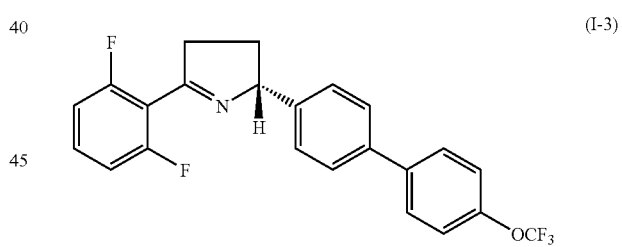

Conversion of N-Boc-Aminoketones of the Formula (IV) in to Pyrrolines of the Formula (I)

(I-3)

At 0° C., compound (IV-1) (0.10 g, 0.19 mmol) is initially charged in dichloromethane (5 ml). Trifluoroacetic acid (0.14 ml, 18.7 mmol) is added dropwise and the reaction mixture is stirred at room temperature for 3 h and then concentrated to dryness. The residue is taken up in dichloromethane and adjusted to pH 12 using 2 M NaOH. The organic phase is washed with water, dried over magnesium sulphate, filtered and concentrated under reduced pressure.

This gives 0.09 g (~100% of theory) of (2R)-5-(2,6-difluorophenyl)-2-[4'-(trifluoromethoxy)-1,1'-biphenyl-4-yl]-3,4-dihydro-2H-pyrrole (I-3).

HPLC: log P (pH 2.3)=4.13 (purity 90.4%);

Optical rotation: $[\alpha]_D$=+33.9 (c=0.9, MeOH); 20° C.;

Enantiomeric excess (ee value): 99.0%.

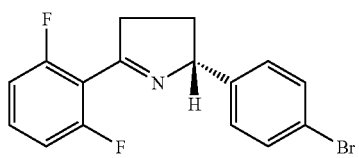
(I-15)

At 0° C., compound (IV-2) (0.65 g, 75.3% pure) is initially charged in dichloromethane (20 ml). Trifluoroacetic acid (1.08 ml, 14.0 mmol) is added dropwise, and the reaction mixture is stirred at room temperature for 3 h and then concentrated to dryness. The residue is taken up in ethyl acetate and adjusted to pH 11 using 1 M NaOH. The organic phase is washed with water, dried over magnesium sulphate, filtered and concentrated under reduced pressure. The crude product is purified by silica gel chromatography (mobile phase: cyclohexane/ethyl acetate, 8:1 v/v).

This gives 0.19 g (53% of theory) of (2R)-2-(4-bromophenyl)-5-(2,6-difluorophenyl)-3,4-dihydro-2H-pyrrole (I-15).

HPLC: log P (pH 2.3)=2.74 (purity 96.69%);

Enantiomeric excess (ee value): 99.9%.

The following compounds are synthesized analogously:

Phases of this type are described, for example, in EP-A 0 379 917. Under the conditions given above, the dextrirotatory enantiomer elutes first.

Stationary phase: 1000 g of silica gel CSP; 10 µm, as described above

Column: 450 mm×75 mm

Eluent: Ethyl acetate

Flow rate: 100 ml/min

UV detection: 254 nm

Sample application: 6 g of racemate (=150 ml of a solution of 40 g of racemate in 1 l of ethyl acetate)

The chromatographic separation conditions are set such that elution of the second enantiomer is accelerated by a short gradient with 100% methanol, thus reducing the total elution time considerably.

Following analysis for enantiomeric purity, the appropriate eluate fractions are pooled and substantially concentrated under reduced pressure and the residues are filtered off and, after washing with n-heptane, dried.

| No. | Structure | Optical rotation [α]$_D$ | log P (pH 2.3) |
|---|---|---|---|
| I-16 | ![structure] | +34.1 (c = 0.92, CHCl$_3$); 20° C. | 3.55 |
| I-17 | ![structure] | +48.9 (c = 0.94, MeOH); 20° C. | 2.85 |

Process γ

Preparation of the Optically Active Lactams of the Formula (VII) by Racemate Resolution The racemate is resolved at room temperature by liquid chromatography on the chiral stationary polyamide silica gel phase using the eluent ethyl acetate and photometric detection. The chiral phase used is based on the monomer N-methacryloyl-L-leucine-d-menthylamide which, after free-radical polymerization, is covalently attached to a modified silica gel.

The enantiomeric purities of the lactams of the formula (VII) are determined by HPLC as follows:

Column: CSP analogously to the preparative separation (10 µm; 250×4.6 mm)

Eluent: Ethyl acetate/methanol 25:1 (v/v)

Flow rate: 1 mil/min

UV detection: 280 nm

The following lactams of the formula (Vet) are obtained by Process γ:

| No. | Structure | Optical rotation | ee value |
|---|---|---|---|
| VII-1 | [pyrrolidinone-biphenyl-OCF₃ structure] | +18.5 (c = 1.5, CHCl₃); 20° C. | 99.9% |
| VII-3 | [pyrrolidinone-biphenyl-SCF₃ structure] | +23.2 (c = 0.5, MeOH); 20° C. | 99.4% |
| VII-4 | [pyrrolidinone-biphenyl-CN structure] | +23.7 (c = 0.7, MeOH); 20° C. | 98.0% |
| VII-5 | [pyrrolidinone-biphenyl-OCF₂CF₂H structure] | +22.8 (c = 0.9, MeOH); 20° C. | 99.4% |
| VII-6 | [pyrrolidinone-biphenyl-OSO₂CF₃ structure] | +26.0 (c = 0.5, MeOH); 20° C. | 99.0% |

Process δ: Asymmetric Synthesis of Lactams of the Formula (VII)

(3S,7aS)-3-Phenyl-7a-[4'-(trifluoromethoxy)-1,1'-biphenyl-4-yl]tetrahydroiyrrolo-[2,1-b][1,3]oxazol-5(6H)-one (IX-1)

Using a Dean-Stark separator, 4-oxo-4-[4'-(trifluoromethoxy)-1,1'-biphenyl-4-yl]butyric acid (VIII-1) (1.00 g, 32.5 mmol), 2(S)-2-amino-2-phenylethanol (4.46 g, 32.5 mmol), 4-toluenesulphonic acid (1.10 g, 5.8 mmol) and toluene (400 ml) are heated under reflux for 3.5 h. The reaction mixture is cooled, filtered and concentrated. The residue is saturated with diisopropyl ether and filtered off with suction.

Yield: 5.56 g, 39% of theory;
HPLC: log P (pH 2.3)=4.55 (purity 92.8%);
Optical rotation: $[\alpha]_D$=+75.8 (c=0.9, MeOH); 20° C.;
Melting point: 104° C.

(3S,7aS)-7a-(4-Bromophenyl)-3-phenyltetrahydropyrrolo[2,1-b][1,3]oxazol-5(6H)-one (IX-2)

Using a Dean-Stark separator, 3-(4-bromobenzoyl)-propionic acid (VIII-2) (18.75 g, 72.9 mmol), 2(S)-2-amino-2-phenylethanol (10.0 g, 72.9 mmol), 4-toluenesulphonic acid (2.47 g, 13.0 mmol) and toluene (400 ml) are heated under reflux for 3.5 h. The reaction mixture is cooled, filtered and concentrated under reduced pressure. The crude product is purified by silica gel chromatography (mobile phase: cyclohexane/ethyl acetate, 6:1 v/v).

Yield: 15.47 g, 55% of theory;
HPLC: log P (pH 2.3)=3.36 (purity 92.3%);
Optical rotation: $[\alpha]_D$=+82.0 (c=1.0, MeOH); 20° C.;
Melting point: 111-113° C.

(5R)-1-[(1S)-2-Hydroxy-1-phenylethyl]-5-[4'-(trifluoromethoxy)-1,1'-biphenyl-4-yl]-2-pyrrolidinone (X-1)

Compound (IX-1) (3.81 g, 8.7 mmol) is initially charged in dichloromethane (75 ml) and, at −78° C., triethylsilane (3.37 g, 29 mmol) and TiCl₄ (1 M solution in CH₂Cl₂, 19.1 ml, 19 mmol) are successively added dropwise. The mixture is stirred at −78° C. for 2 h and then at room temperature overnight. The reaction mixture is cooled to 0° C. and saturated aqueous ammonium chloride solution (100 ml) is added dropwise. The organic phase is washed with water, dried over sodium sulphate, filtered and concentrated under reduced pressure. The crude product is reacted further without additional purification.

Yield: 3.63 g (95% of theory);
HPLC: log P (pH 2.3)=3.80 (purity 96.9%).

(5R)-5-(4-Bromophenyl)-1-[(1S)-2-hydroxy-1-phenylethyl]-2-pyrrolidinone (X-2)

Compound (IX-2) (3.12 g, 8.7 mmol) is initially charged in dichloromethane (75 ml) and, at −78° C., triethylsilane (3.37 g, 29 mmol) and TiCl₄ (1 M solution in CH₂Cl₂, 19.1 ml, 19 mmol) are successively added dropwise. The mixture is stirred at −78° C. for 2 h, and then at room temperature overnight. The reaction mixture is cooled to 0° C. and saturated aqueous ammonium chloride solution (100 ml) is added dropwise. The organic phase is washed with water, dried over sodium sulphate, filtered and concentrated under reduced pressure. The crude product is reacted further without additional purification.

Yield: 3.12 g (~100% of theory);
HPLC: log P (pH 2.3)=2.58 (purity 100%);
Optical rotation: $[\alpha]_D$=+40.0 (c=1.0, MeOH); 20° C.

(5R)-1-[(1S)-2-Chloro-1-phenylethyl]-5-[4'-(trifluoromethoxy)-1,1'-biphenyl-4-yl]-2-pyrrolidinone (XI-1)

Compound (X-1). (0.44 g, 1.0 mmol) is initially charged in THF (10 ml), and thionyl chloride (0.29 g, 2.42 mmol) is added dropwise. The reaction mixture is stirred for 1.5 h and concentrated. The crude product is reacted further without additional purification.

Yield: 0.38 g (83% of theory)
HPLC: log P (pH 2.3)=4.78 (purity 93.1%).

(5R)-5-(4-Bromophenyl)-1-[(1S)-2-chloro-1-phenylethyl]-2-pyrrolidinone (XI-2)

Compound (X-2) (2.00 g, 5.0 mmol) is initially charged in THF (10 ml), and thionyl chloride (1.19 g, 10.0 mmol) is added dropwise. The reaction mixture is stirred for 1.5 h and concentrated. The crude product is reacted further without additional purification.

Yield: 1.69 g (82% of theory)
HPLC: log P (pH 2.3)=3.61 (purity 91.8%)
Optical rotation: $[\alpha]_D$=+42.0 (c=0.85, MeOH); 20° C.

(5R)-1-(1-Phenylvinyl)-5-[4'-(trifluoromethoxy)-1,1'-biphenyl-4-yl]-2-pyrrolidinone (XII-1)

Compound (XI-1) (0.50 g, 1.1 mmol) is initially charged in tBuOH (5 ml), and KOtBu (0.26 g, 2.4 mmol) is added. The reaction mixture is stirred at 60° C. overnight, cooled and concentrated. The residue is taken up in ethyl acetate and washed successively with 1 M HCl and water. The organic phase is dried over magnesium sulphate, filtered and concentrated. The crude product is reacted further without additional purification.

Yield: 0.34 g (74% of theory)
HPLC: log P (pH 2.3)=4.35 (purity 98.4%).

(5R)-5-(4-Bromophenyl)-1-(1-phenylvinyl)-2-piyrrolidinone (XII-2)

Compound (XI-2) (1.00 g, 2.6 mmol) is initially charged in tBuOH (10 ml), and KOtBu (0.64 g, 5.7 mmol) is added. The reaction mixture is stirred at 60° C. overnight, cooled and concentrated. The residue is taken up in ethyl acetate and washed successively with 1 M HCl and water. The organic phase is dried over magnesium sulphate, filtered and concentrated. The crude product is reacted further without additional purification.

Yield: 0.67 g (34% of theory)
HPLC: log P (pH 2.3)=3.18 (purity 45.75%).

(5R)-5-[4'-(Trifluoromethoxy)-1,1'-biphenyl-4-yl]-2-pyrrolidinone (VII-1)

Compound (XII-1) (0.98 g, 2.3 mmol) is initially charged in THF (5 ml). 1 M HCl (5 ml) is added, the reaction mixture is stirred at 60° C. for 1 h and cooled to room temperature, and ethyl acetate (100 ml) is added. The organic phase is washed successively with saturated aqueous sodium bicarbonate solution and brine, dried over magnesium sulphate, filtered and concentrated. The crude product is reacted further without additional purification.

Yield: 0.51 g (74% of theory)
HPLC: log P (pH 2.3)=2.95 (purity 77.9%)
Enantiomeric excess (ee value): 97.1% (using Method 1 for lactams).

(5R)-5-(4-Bromophenyl)-2-pyrrolidinone (VII-2)

Compound (XII-2) (0.57 g, 1.7 mmol) is initially charged in THF (3 ml). 1 M HCl (3 ml) is added, and the reaction mixture is stirred at 60° C. for 1 h, cooled to room temperature and concentrated. The residue is taken up in in dichloromethane (30 ml) and, at 0° C., adjusted to pH 11 using 1 N NaOH. The organic phase is washed with water, dried over magnesium sulphate, filtered and concentrated. The crude product is reacted further without additional purification.

Yield: 0.36 g (84% of theory)
HPLC: log P (pH 2.3)=3.54 (purity 95.3%)
Optical rotation: $[\alpha]_D$=+33.6 (c=1.0, MeOH); 20° C.
Enantiomeric excess (ee value): 99.8% (using Method 1 for lactams).

Process ε: Asymmetric Synthesis of Lactams of the Formula (VII)

Methyl-4-oxo-4-[4'-(trifluoromethoxy)-1,1'-biphenyl-4-yl]butanoate (VIII-a-1)

Crude 4-oxo-4-[4'-(trifluoromethoxy)-1,1'-biphenyl-4-yl] butyric acid (25 g, content: 65%, GC, silylated, 100% method) is dissolved in a mixture of methanol (50 ml) and 2,2-dimethoxypropane (11.5 g, 110 mmol), treated with trimethylsilyl chloride (0.75 g, 7 mmol) and stirred at 50° C. for 16 h. The reaction mixture is then concentrated and the residue is recrystallized from toluene.

Yield: 18.2 g
HPLC: log P (pH 2.3)=4.01.

N-Allyl-4-oxo-4-[4'-(trifluoromethoxy)-1,1'-biphenyl-4-yl]butanamide (XV-1)

Methyl-4-oxo-4-[4'-(trifluoromethoxy)-1,1'-biphenyl-4-yl]butanoate (VIII-a-1) (18.2 g, 52 mmol) is treated with allylamine (41.6 g, 730 mmol) and ammonium chloride (1.8 g, 33 mmol) and heated under reflux for 6 h. For work-up, the mixture is poured into ice-cold aqueous HCl (2 M) and extracted with ethyl acetate. The combined organic phases are dried ($Na_2SO_4$) and concentrated. The crude product (17.7 g, content: 84.5%, HPLC, 100% method) is recrystallized from toluene.

Yield: 8.6 g
HPLC: log P (pH 2.3)=3.34, 3.42.

(4S)-N-Allyl-4-hydroxy-4-[4'-(trifluoromethoxy)-1,1'-biphenyl-4-yl]butanamide (XVI-1)

Under argon, the anhydrous N-allyl-4-oxo-4-[4'-(trifluoromethoxy)-1,1'-biphenyl-4-yl]butanamide (XV-1) (2.26 g, 6 mmol) is, in a Schlenk tube which had been dried by heating, dissolved in anhydrous THF (40 ml) and, at 0° C., treated with a solution of (3aR)-1-methyl-3,3,6-triphenyltetrahydro-3H-pyrrolo[1,2-c][1,3,2]oxazaborole (600 µl, 1 M in toluene). At 0° C., a solution of the $BH_3$*$SMe_2$ complex (7.1 ml, 0.59 M) is added dropwise over a period of 30 min to this solution. The mixture is stirred at 0° C. for 1 h. The ice-bath is removed, and the mixture is then stirred at room temperature for another 6 h. MeOH (10 ml) is added carefully and the mixture is then concentrated. For work-up, the residue is filtered through silica gel 60 (mobile phase: $CH_3OH/CH_2Cl_2$, 10:1).

Yield: 1.24 g
HPLC: log P (pH 2.3)=2.99
Enantiomeric excess (ee value): 87% (GC method).

(5R)-1-Allyl-5-[4'-(trifluoromethoxy)-1,1'-biphenyl-4-yl]-2-pyrrolidinone (XVII-1)

Under argon, KOtBu (0.64 g, 5.7 mmol) is suspended, in a Schlenk tube which had been dried by heating, in THF (5 ml, anhydrous). At 0° C., a solution of (4S)-N-allyl-4-hydroxy-4-[4'-(trifluoromethoxy)-1,1'-biphenyl-4-yl]butanamide (XVI-1) (0.99 g, 2.6 mmol) in THF (8 ml, anhydrous) is added dropwise. The reaction mixture is stirred at 0° C. for 1 h and a solution of tosyl chloride (0.52 g, 2.7 mmol) in THF (5 ml, anhydrous) is then added dropwise over a period of 20 min. The mixture is stirred at 0° C. for 2 h and at room temperature for 16 h. For work-up, the mixture is admixed with water, adjusted to pH 5 using HCl and extracted with ethyl acetate. The combined organic phases are dried ($Na_2SO_4$) and concentrated. The residue (0.85 g, content: 81%, HPLC, 100% method) is further purified by flash chromatography (mobile phase: ethyl acetate/petroleum ether (40/60), 1:1).

Yield: 0.55 g
HPLC: log P (pH 2.3)=3.88
Enantiomeric excess (ee value): 85% (GC method).

(5R)-5-[4'-(Trifluoromethoxy)-1,1'-biphenyl-4-yl]-2-pyrrolidinone (VII-1)

Under argon, (5R)-1-allyl-5-[4'-(trifluoromethoxy)-1,1'-biphenyl-4-yl]-2-pyrrolidinone (XVII-1) (0.41 g, 1.14 mmol) is initially charged in a Schlenk tube together with $Pd[PPh_3]_4$ (131.7 mg, 0.114 mmol) and p-toluenesulphonic acid hydrate (0.52 g, 2.74 mmol), and THF (2 ml, degassed) and 1 ml of $H_2O$ are added. The yellow suspension is heated under reflux for 3 h. For work-up, the mixture, which was cooled to room temperature, is diluted with $NaHCO_3$ solution and admixed with ethyl acetate and filtered through kieselguhr. The combined organic phases are dried ($Na_2SO_4$) and concentrated under reduced pressure.

Yield: 0.5 g (89% of theory)
HPLC: log P (pH 2.3)=3.00
Enantiomeric excess (ee value): 85% (using Method 2 for lactams).

A sample of the lactam which had been purified by chromatography was recrystallized from petroleum ether (40/60)/toluene.

Melting point: 164° C.
HPLC: purity 99%
Enantiomeric excess (ee value): 99% (using Method 2 for lactams).

The log P values given in the tables and Preparation Examples above are determined in accordance with EEC Directive 79/831 Annex V.A8 by HPLC (High Performance Liquid Chromatography) using a reversed-phase column (C 18). Temperature: 43° C.

The determination was carried out in the acidic range at pH 2.3 using the mobile phases 0.1% aqueous phosphoric acid and acetonitrile; linear gradient from 10% acetonitrile to 90% acetonitrile.

Calibration was carried out using unbranched alkan-2-ones (having 3 to 16 carbon atoms) with known log P values (determination of the log P values by the retention times using linear interpolation between two successive alkanols).

The lambda max values were determined in the maxima of the chromatographic signals using the UV spectra from 200 nm to 400 nm.

The enantiomeric purity of the pyrrolines of the formula (I) was determined by analytical HPLC using the following conditions:

Stationary phase: Chiralcel OD® (Daicel, Japan); 5 µm
Column: 250 mm×4.6 mm (I.D.)
Eluent: n-heptane/2-propanol 10:1
Flow rate: 1 ml/min
UV detection: 254 nm The enantiomeric purity of the lactams of the formula (VII) was determined by analytical HPLC using the following conditions (Method 1):

Stationary phase: Silica gel-CSP; 10 µm
Column: 250 mm×4.6 mm (I.D.)
Eluent: Ethyl acetate/methanol 25:1 (v/v)
Flow rate: 1 ml/min
UV detection: 280 nm The enantiomeric purity of the lactams of the formula (VII) was determined by analytical HPLC using the following conditions (Method 2):

Stationary phase: Chiralcel OD-H® (Daicel, Japan); 5 µm
Column: 250 mm×4.6 mm (I.D.)
Eluent: n-heptane/2-propanol 19:1 (v/v)
Flow rate: 0.5 ml/min
UV detection: 220 nm The enantiomeric purity of the butanamides of the formula (XVI) and the pyrrolidinones of the formula (XVII) was determined by analytical GC using the following conditions:

Stationary phase: Hydrodex-β-6TBDM
Column: 25 m×0.25 mm (I.D.)
Carrier gas: Helium
Pressure: 120 kPa
Injector temperature: 220° C.
Detector: FID
Temperature prog.: 13 min 120° C., 1° C./min to 220° C.

USE EXAMPLES

Example A

*Heliothis Armigera* Test

| Solvent: | 30 parts by weight of dimethylformamide |
|---|---|
| Emulsifier: | 1 part by weight of alkylaryl polyglycol ether |

To prepare a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with caterpillars of the cotton bollworm (*Heliothis armigera*) while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE A
Plant-damaging insects
Heliothis armigera test
| Active compound | | Concentration of active compound in ppm | Kill rate in % after 6 d |
|---|---|---|---|
| 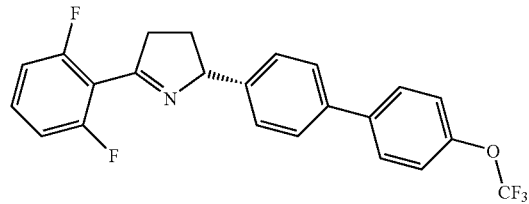<br>(R)-configuration | according to the invention | 8 | 100 |
| 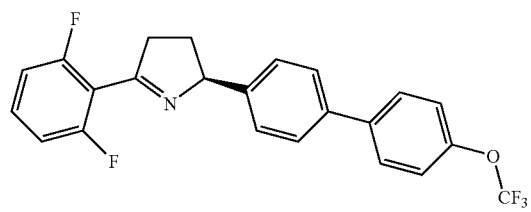<br>(S)-configuration | comparative substance | 8 | 0 |
| 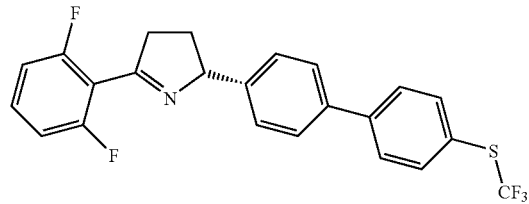<br>(R)-configuration | according to the invention | 1.6 | 100 |
| 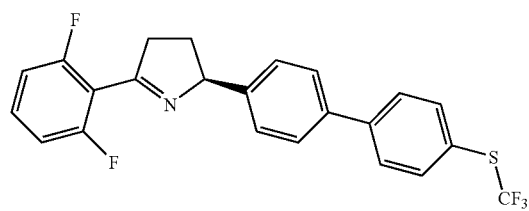<br>(S)-configuration | comparative substance | 1.6 | 0 |

Example B

*Heliothis Virescens* Test

| | |
|---|---|
| Solvent: | 30 parts by weight of dimethylformamide |
| Emulsifier: | 1 part by weight of alkylaryl polyglycol ether |

To prepare a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with *Heliothis virescens* caterpillars while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE B

Plant-damaging insects
Heliothis virescens test

| Active compound | | Concentration of active compound in ppm | Kill rate in % after 6 d |
|---|---|---|---|
| [structure, rac.] | known | 0.32 | 20 |
| [structure, (R)-configuration] | according to the invention | 0.32 | 90 |
| [structure, (S)-configuration] | comparative substance | 8 | 0 |

TABLE B-continued

Plant-damaging insects
Heliothis virescens test

| Active compound | | Concentration of active compound in ppm | Kill rate in % after 6 d |
|---|---|---|---|
| [structure: 2,6-difluorophenyl-dihydropyrrole-biphenyl-SCF₃, (R)-configuration] | according to the invention | 1.6 | 100 |
| [structure: 2,6-difluorophenyl-dihydropyrrole-biphenyl-SCF₃, (S)-configuration] | comparative substance | 1.6 | 15 |
| [structure: 2,6-difluorophenyl-dihydropyrrole-biphenyl-O-CHF₂CF₃, (R)-configuration] | according to the invention | 8 | 100 |
| [structure: 2,6-difluorophenyl-dihydropyrrole-biphenyl-O-CHF₂CF₃, (S)-configuration] | comparative substance | 8 | 0 |
| [structure: 2,6-difluorophenyl-dihydropyrrole-biphenyl-O-C(=CF₂)CF₃, (R)-configuration] | according to the invention | 40 | 100 |

Example C

*Plutella* Test

| | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*) while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE C

Plant-damaging insects
Plutella test

| Active compound | | Concentration of active compound in ppm | Kill rate in % after 6 d |
|---|---|---|---|
| 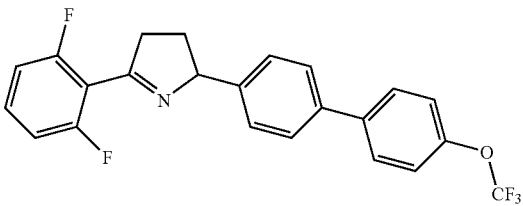 rac. | known | 0.01 | 0 |
| 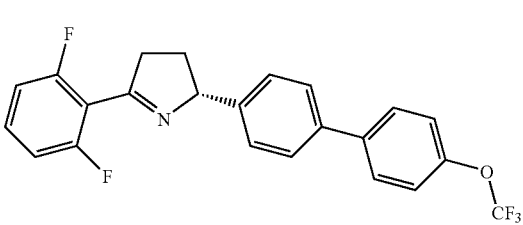 (R)-configuration | according to the invention | 0.01 | 100 |
| 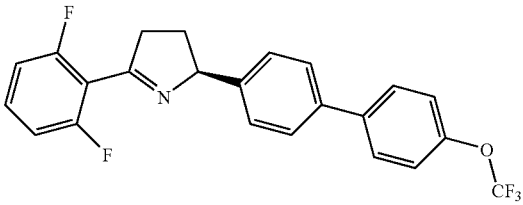 (S)-configuration | comparative substance | 1.6 | 0 |
| 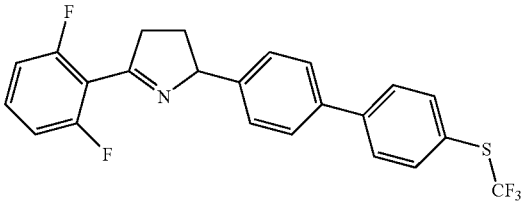 rac. | known | 0.0128 | 45 |

TABLE C-continued

Plant-damaging insects
Plutella test

| Active compound | | Concentration of active compound in ppm | Kill rate in % after 6 d |
|---|---|---|---|
| [2,6-difluorophenyl-dihydropyrrole-biphenyl-SCF₃, (R)-configuration] | according to | 0.0128 | 45 |
| [2,6-difluorophenyl-dihydropyrrole-biphenyl-SCF₃, (S)-configuration] | comparative substance | 1.6 | 5 |
| [2,6-difluorophenyl-dihydropyrrole-biphenyl-OCH(CF₃)(CHF₂), (R)-configuration] | according to the invention | 0.32 | 100 |
| [2,6-difluorophenyl-dihydropyrrole-biphenyl-OCH(CF₃)(CHF₂), (S)-configuration] | comparative substance | 0.32 | 0 |
| [2,6-difluorophenyl-dihydropyrrole-biphenyl-OC(CF₃)=CF₂, (R)-configuration] | according to the invention | 0.064 | 100 |

Example D

*Spodoptera Exigua* Test

| | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera exigua*) while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE D

Plant-damaging insects
Spodoptera exigua test

| Active compound | | Concentration of active compound in ppm | Kill rate in % after 6 d |
|---|---|---|---|
| 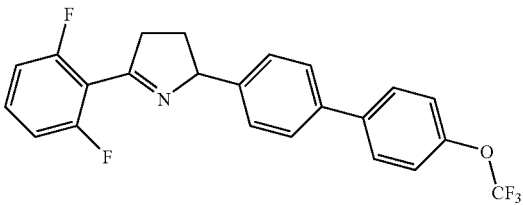 rac. | known | 0.04 | 55 |
| 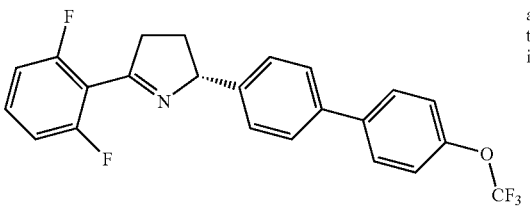 (R)-configuration | according to the invention | 0.04 | 100 |
| 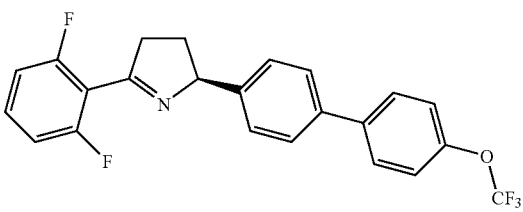 (S)-configuration | comparative substance | 8 | 0 |
| 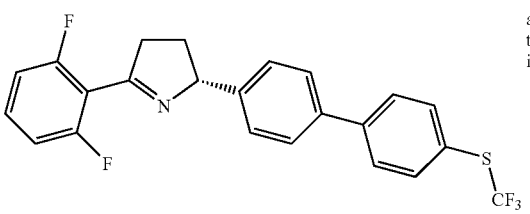 (R)-configuration | according to the invention | 1.6 | 100 |

TABLE D-continued

Plant-damaging insects
Spodoptera exigua test

| Active compound | | Concentration of active compound in ppm | Kill rate in % after 6 d |
|---|---|---|---|
| (S)-configuration — [2,6-difluorophenyl-dihydropyrrole-biphenyl-S-CF₃] | comparative substance | 1.6 | 0 |
| (R)-configuration — [2,6-difluorophenyl-dihydropyrrole-biphenyl-O-CHF₂-CF₃] | according to the invention | 1.6 | 100 |
| (S)-configuration — [2,6-difluorophenyl-dihydropyrrole-biphenyl-O-CHF₂-CF₃] | comparative substance | 1.6 | 0 |
| (R)-configuration — [2,6-difluorophenyl-dihydropyrrole-biphenyl-O-CF₂=CF₃] | according to the invention | 8 | 100 |

Example E

*Spodoptera Frugiperda* Test

| | |
|---|---|
| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

Active compounds, active compound concentrations and test results are shown in the table below.

TABLE E

Plant-damaging insects
*Spodoptera frugiperda* test

| Active compound | Concentration of active compound in ppm | Kill rate in % after 6 d |
|---|---|---|
| 2-CH₃-C₆H₄ / biphenyl-OCF₃ dihydropyrrole | 0.02 | 25 |
| 2-Cl-C₆H₄ / biphenyl-OCF₃ dihydropyrrole | 0.02 | 100 |
| 2,6-F₂-C₆H₃ / biphenyl-OCF₃ dihydropyrrole | 8 | 0 |
| 2,6-F₂-C₆H₃ / biphenyl-SCF₃ dihydropyrrole | 0.0128 | 20 |
| 2,6-F₂-C₆H₃ / biphenyl-OCF₂CF₂H dihydropyrrole | 0.0128 | 65 |
| 2,6-F₂-C₆H₃ / biphenyl-O-CF=CF₂ dihydropyrrole | 1.6 | 10 |
| 2,6-F₂-C₆H₃ / (3-EtO-4-iPr-phenyl) dihydropyrrole | 1.6 | 100 |
| 2,6-F₂-C₆H₃ / biphenyl-S(O)CF₃ dihydropyrrole | 1.6 | 0 |

TABLE E-continued

Plant-damaging insects
*Spodoptera frugiperda* test

| Active compound | Concentration of active compound in ppm | Kill rate in % after 6 d |
|---|---|---|
| 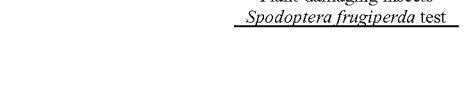 | 1.6 | 100 |

Example F

*Tetranyhcus* Test (OP-resistant/Dip Treatment)

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse rat spider mite (*Tetranychus urticae*) are dipped into the preparation of active compound of the desired concentration.

After the desired period of time, the efficacy in % is determined. 100% means that all spider mites have been killed; 0% means that none of the spider mites have been killed.

Active compounds, active compound concentrations and test results are shown in the table below.

TABLE F

Plant-damaging mites
Tetranychus test (OP-resistant/dip treatment)

| Active compound | Concentration of active compound in ppm | Kill rate in % after 7 d |
|---|---|---|
| 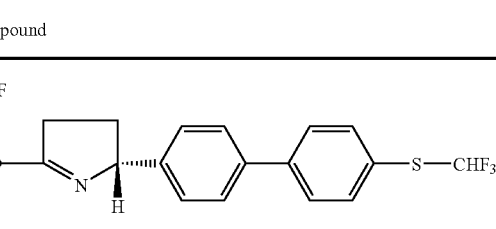 | 0.32 | 0 |
| 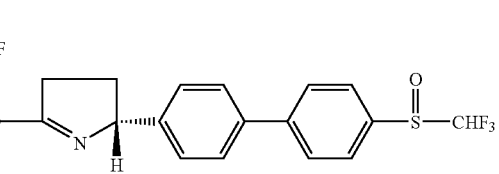 | 0.32 | 90 |
|  | 8 | 0 |

TABLE F-continued

Plant-damaging mites
Tetranychus test (OP-resistant/dip treatment)

| Active compound | Concentration of active compound in ppm | Kill rate in % after 7 d |
|---|---|---|
| 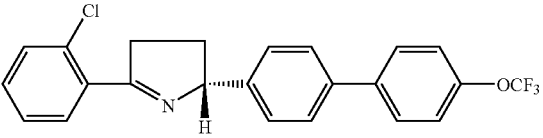 | 0.0128 | 95 |
| 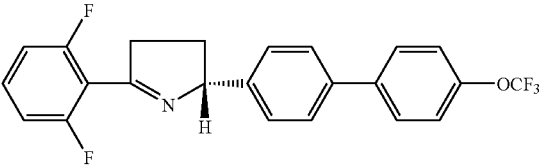 | 0.0128 | 0 |
| 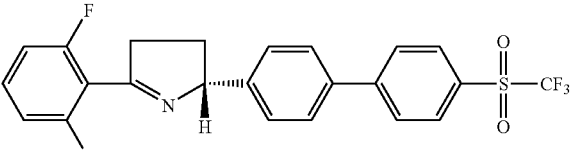 | 0.01 | 98 |

Example G

Diabrotica Balteata Test (Larvae in Soil)

Critical Concentration Test/Soil Insects—Treatment of Transgenic Plants

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured on to the soil. Here, the concentration of active compound in the preparation is virtually irrelevant, only the amount by weight of active compound per volume unit of soil, which is stated in ppm (mg/l), matters. The soil is filled into 0.25 l pots and these are allowed to stand at 20° C.

Immediately after preparation, 5 pre-germinated maize corns of the cultivar YIELD GUARD (trade mark of Monsanto Comp., USA) are placed into each pot. After 2 days, the test insects in question are placed into the treated soil. After a further 7 days, the efficacy of the active compound is determined by counting the maize plants that have emerged (1 plant=20% efficacy).

Example H

Heliothis Virescens Test (Treatment of Transgenic Plants)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade name of Monsanto Comp. USA) are treated by being dipped into the preparation of active compound of the desired concentration and are populated with the tobacco bud worm *Heliothis virescens* while the leaves are still moist.

After the desired period of time the kill in % is determined. 100% means that all caterpillars have been killed; 0% means that none of the caterpillars have been killed.

Example I

Amblyomma Hebraeum (ER) (Polyphargous Tick Nymphs/Dip Treatment)

| Test animals: | *Amblyomma hebraeum* nymphs which have sucked themselves full |
|---|---|
| Solvent: | Dimethyl sulphoxide |

20 mg of active compound are dissolved in 1 ml of dimethyl sulphoxide. To prepare a suitable formulation, the solution of active compound is diluted with water to the concentration desired in each case.

10 nymphs which have sucked themselves full are immersed for 1 min in the preparation of active compound to be tested. The animals are transferred to petri dishes (⌀ 9.5 cm) fitted with filter paper discs and covered. After the nymphs have remained in a controlled-environment cabinet for 4 weeks, the ecdysis rate is determined.

100% means that none of the animals have undergone normal ecdysis. 0% means that all animals have undergone ecdysis.

Active compounds, active compound concentrations and test results are shown in the table below.

Example K

*Amblyomma hebraeum* (EH) (Polyphargous Tick Nymphs/Dip Treatment, Determination of the ED50)

| Test animals: | *Amblyomma hebraeum* nymphs which have sucked themselves full |
|---|---|
| Solvent: | Dimethyl sulphoxide |

TABLE I

*Amblyomma hebraeum* (EH)
(polyphargous tick nymphs/dip treatment)

| Active compound | Concentration of active compound in ppm | Effects on ecdysis in % |
|---|---|---|
| [structure: 2,6-difluorophenyl-dihydropyrrole-biphenyl-S-CHF$_3$] | 10 | 100 |
| [structure: 2,6-difluorophenyl-dihydropyrrole-biphenyl-S(=O)-CHF$_3$] | 10 | 100 |
| [structure: 2,6-difluorophenyl-dihydropyrrole-biphenyl-S(=O)$_2$-CHF$_3$] | 10 | 0 |
| [structure: 2-methylphenyl-dihydropyrrole-biphenyl-OCF$_3$] | 10 | 100 |
| [structure: 2-chlorophenyl-dihydropyrrole-biphenyl-OCF$_3$] | 10 | 100 |
| [structure: 2,6-difluorophenyl-dihydropyrrole-biphenyl-OCF$_3$] | 10 | 0 |

20 mg of active compound are dissolved in 1 ml of dimethyl sulphoxide. To prepare a suitable preparation, the solution of active compound is diluted with water to the concentration desired in each case.

For the determination of the ED50 value, a dose-activity curve with the concentration spectrum 1000, 300, 100, 30, 10, 3, 1, 0.3, 0.1, 0.03, 0.01 ppm is prepared.

10 nymphs which have sucked themselves full are immersed for 1 min into the preparation of active compound to be tested. The animals are transferred to petri dishes (∅ 9.5 cm) fitted with filter paper discs and covered. After the nymphs have remained in a controlled-environment cabinet for 4 weeks, the ecdysis rate is determined.

100% means that none of the animals have undergone normal ecdysis. 0% means that all animals have undergone ecdysis.

The data are calculated by a 4-parameter logistic curve fit using XLfit (ID Business Solutions Ltd.). If at 1000 ppm 50% mortality has not been reached, the ED50 is judged to be not determinable.

Active compounds and test results are shown in the table below.

TABLE K

*Amblyomma hebraeum* (EH)
ED50 determination
(polyphargous tick nymphs/dip treatment)

| Active compound | ED 50 (ppm) |
|---|---|
| [structure: 2,6-difluorophenyl-pyrroline-biphenyl-S-CHF₃] | 0.27 |
| [structure: 2,6-difluorophenyl-pyrroline-biphenyl-S(O)-CHF₃] | 0.14 |
| [structure: 2,6-difluorophenyl-pyrroline-biphenyl-S(O)₂-CHF₃] | not determinable |
| [structure: 2-methylphenyl-pyrroline-biphenyl-OCF₃] | 0.58 |
| [structure: 2-chlorophenyl-pyrroline-biphenyl-OCF₃] | 0.20 |
| [structure: 2,6-difluorophenyl-pyrroline-biphenyl-OCF₃] | 549.86 |

What is claimed is:
1. An optically active Δ¹-pyrroline of the formula (I) having the formula
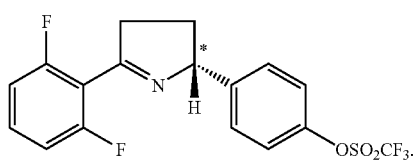
2. An optically active Δ¹-pyrroline of the formula (I) having the formula
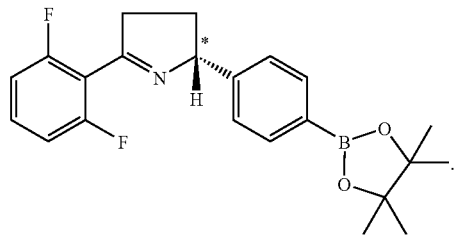
* * * * *